United States Patent [19]

Castano

[11] Patent Number: 5,713,353

[45] Date of Patent: Feb. 3, 1998

[54] OPTICAL METHOD AND DEVICE FOR DETERMINING BLOOD GLUCOSE LEVELS

[76] Inventor: Jaime A. Castano, 1931 Ralston Ave., Richmond, Calif. 94805

[21] Appl. No.: 634,849

[22] Filed: Apr. 19, 1996

[51] Int. Cl.$^6$ ...................................................... A61B 5/00
[52] U.S. Cl. .......................................... 128/633; 128/630
[58] Field of Search ..................................... 128/630, 633, 128/645, 745, 897, 898; 351/206; 356/39

[56] References Cited

U.S. PATENT DOCUMENTS

| | | |
|---|---|---|
| 3,761,921 | 9/1973 | Adler et al. . |
| 3,807,839 | 4/1974 | Sugarman et al. . |
| 3,814,510 | 6/1974 | Adler et al. . |
| 3,963,019 | 6/1976 | Quandt . |
| 4,012,128 | 3/1977 | Regan . |
| 4,014,321 | 3/1977 | March . |
| 4,324,460 | 4/1982 | Daley . |
| 4,750,830 | 6/1988 | Lee . |
| 4,789,234 | 12/1988 | Ginsburg et al. . |
| 4,832,480 | 5/1989 | Komacker et al. . |
| 5,065,767 | 11/1991 | Maddess . |
| 5,086,229 | 2/1992 | Rosenthal et al. . |
| 5,209,231 | 5/1993 | Cote et al. . |
| 5,223,865 | 6/1993 | Shirao et al. . |
| 5,398,681 | 3/1995 | Kupershmidt . |
| 5,433,197 | 7/1995 | Stark . |
| 5,448,992 | 9/1995 | Kupershmidt . |
| 5,485,230 | 1/1996 | Zimmerman . |

OTHER PUBLICATIONS

Barlow, R.B., Jr., Boudreau, E.A. and Pelli, D.G. 1993. "Metabolic Modulation of Human Visual Sensitivity," *Invest. Ophthamol. Vis. Sci. Suppl.* 43:785.

Kaplan, E. et al., 1988. "Color and Luminace Contrast as Tools for Probing the Primate Retina," *Neurosci. Res. Suppl.* 8:S151.

Macaluso, C., Onoe, S. and Niemeyer, G. 1992. "Changes in Glucose Level Affect Rod Function More than Cone Function in the Isolated, Perfused Cat Eye." *Invest. Ophthalmol. Vis. Sci.* 33(10):2798–808.

McFarland, R.A. and Forbes, W.H. 1940. "The Effects of Variations in the Concentration of Oxygen and Glucose Adaption." *J. Gen. Physiol.* 24:69.

Purpura, K, Kaplan, E., and Shapley, R.M., 1988. "Background Light and the Contrast Gain of Primate P–and M–Retinal Ganglion Cells." *Proc. Natl. Acad. Sci. USA* 85:4534.

Schiller, P.H. and Logothetis, N.K., 1990. "The Color–opponent and Broad–band Channels of the Primate Visual Sustem," *Trends in Neurosci.* 13:392.

Schneck, M.E. 1996. "Influence of Blood Glucose Level on Chromatic VEP in Type I Diabetes." In: *Vision Science and Its's Applications* Optical Society of America, Washington, D.C., pp. 38–42.

(List continued on next page.)

*Primary Examiner*—John P. Lacyk
*Assistant Examiner*—Bryan K. Yarnell
*Attorney, Agent, or Firm*—Fish & Richardson P.C.

[57] ABSTRACT

Blood glucose levels of a person are determined by a device which provides a changing light pattern which changes in regard to one or several parameters defining its luminance, color, rate of flicker, spatial contrast, detail content, speed or otherwise provided that the change gradually stimulates one retinal system more than another retinal system. A person observes the changing light pattern until a subjective visual effect occurs, which is preferably an observer perceived dramatic change in the appearance of the light pattern, for example a change in the perceived direction of rotation. The subjective visual effect indicates a specific ratio of stimulation of the two retinal systems, for example the point of balanced stimulation of the two systems. Upon noting the subjective visual effect the patient actuates a mechanism which takes note of the current light pattern parameter values, allowing the device to relate such parameter values with a corresponding blood glucose level using predetermined calibration data. Thereby, the person's glucose level is accurately determined in a completely non-invasive manner.

25 Claims, 10 Drawing Sheets

OTHER PUBLICATIONS

Schneck, M.E., Volbrcht, V.J., and Adams, J.J. 1991. "Immediate and Significant changes in SWS Sensitivity Accompany Variations in Blood Glucose in Diabetic Observers". In: *Technical Digest on Noninvasive Assessment of the Visual System.* eds? Optical Society of America, Washington, D.C., vol. 1, pp. 204–207.

Shapley, R., 1990. "Visual Sensitivity and Parallel Retinocortical Channels," *Ann Rev. Psychol.* 41:635–58.

Volbrect. V.J. et al. 1994, "Diabetic Short–Wavelength Sensitivity: Variations with Induced Changes in Blood Glucose Level," *Ophthalmol. Vis. Sci.* 35(3):1243–6.

Winkler, B.S., 1972. "The Electroretinogram of the Isolated Rat Retina," *Vision Res.* 12:1183.

Winkler, B.S., 1975. "Dependence of Rat and Rabbit Photoreceptor Potentials Upon Metaboism in vitro," *Exp. Eye. Res.* 21:545.

OPTICAL METHOD AND DEVICE FOR DETERMINING BLOOD GLUCOSE LEVELS

FIELD OF THE INVENTION

This invention relates generally to the field of optics and more specifically to a method and device for analyzing a patient's perception of a changing light pattern and relating such to the patient's blood glucose level.

BACKGROUND OF THE INVENTION

More than ten million people in the United States of America suffer from diabetes, a deficiency in the body's ability to regulate blood glucose levels. Individuals afflicted with the disease must control their blood glucose levels by measuring their blood glucose levels as frequently as possible and planning accordingly their food intake, level of physical activity and insulin dosage. The measurement of blood glucose levels is done using one of several available invasive techniques.

Invasive techniques require withdrawal of a blood sample from the patient each time an analysis is to be performed. An accurate laboratory blood analysis requires withdrawing from 5 to 10 ml of blood and analyzing it using a laboratory instrument designed for performing such a biochemical analysis. However, the results of the test often are not available for several hours, and sometimes days. In addition, the instruments necessary to perform such an analysis are expensive and require that the blood samples be taken and analyzed by trained technicians.

Another invasive technique, referred to as a "finger poke" or a "finger stick" uses an integrated, self-contained instrument that evaluates a much smaller blood sample (approximately 0.25 ml). The small blood sample is obtained by puncturing a finger with a small lancet. The sample is then placed on a chemically treated carrier and inserted into the instrument. The finger poke devices normally provide the glucose concentration results in a few moments. However, they are still quite costly for private use.

More recently, portable finger poke instruments have become available which require the use of single use, disposable, chemically treated carrier "strips". Although the portable instruments have a relatively low cost (about $100 to $300), cumulative cost to diabetics for the normal supply of disposable carrier "strips" is considerable.

Invasive techniques for glucose analysis are problematic and suffer from poor compliance. Although diabetics can forestall the debilitating and often fatal complications of diabetes by frequent monitoring and control, only a small fraction of diabetics monitor regularly their glucose levels. Diabetics find the current invasive methods of blood glucose monitoring painful, inconvenient and costly. To encourage frequent monitoring and control there is a clear need for a glucose monitor that requires no blood samples, is easy and convenient to use, is portable, and costs less than current methods.

Non-invasive methods for measuring blood glucose have been described. However, to date none of these techniques has resulted in a commercially useful instrument. The non-invasive monitoring methods are roughly divided into measurements based on either (1) the intensity of light being transmitted through or reflected from the tissue ("intensity-sensitive" measurements), (2) the phase shift of modulated light transmitted through the tissue ("phase-sensitive" measurement) or (3) devices which use reverse iontophoretic means to remove substances through the skin as per U.S. Pat. No. 5,279,543 issued Jan. 18, 1994.

When light is transmitted through perfused tissue in vivo, e.g., through a patient's finger, it is differently absorbed by the various components illuminated, namely blood, with its many constituent parts, tissue (including protein, fat, water, cholesterol, etc.), cartilage, and bone. Each component has a specific absorption spectrum, which indicates the absorption at each wavelength of light.

The known intensity sensing methods for measuring the level of a blood constituent, including glucose, are based on measuring an absorption spectrum for blood perfused tissue at two or more different wavelengths, and subtracting therefrom the statistical absorption spectra for each of the various components, except for the one component being measured. It is assumed that after such subtraction, the remainder is the spectrum of the constituent to be measured.

Rosenthal, et al., U.S. Pat. No. 5,086,229 refers to such a non-invasive, near-infrared quantitative analysis instrument for measuring blood glucose. The instrument contains a plurality of near-infrared laser sources having different wavelengths of emission and one or a plurality of photodetectors. A blood-containing body part, e.g., a finger, is placed between the laser sources and photodetectors. The light sources illuminate the body part and the wavelengths transmitted through the body part are detected. The absorption spectra obtained from the photodetector signals are compared with individual statistical absorption spectra of each constituent, which are stored in the memory of the instrument. A glucose level is derived from the comparison.

The non-invasive phase sensitive measurement methods possess significantly higher sensitivity and a much higher signal-to-noise ratio than intensity-measurement methods. The higher sensitivity is the consequence of the noise sources affecting the amplitude, but not the phase, of a signal.

In phase sensitive techniques, an instrument compares a known reference signal, e.g., a sine wave, with a measurement signal that has been passed through the tissue. The measurement signal will have a phase shift relative to the reference signal, and concentrations of blood constituents may be obtained from a measurement of the phase shift.

Cote, et al., "Noninvasive Optical Polarimetric Glucose Sensing Using A True Phase Measurement Technique," *IEEE Transactions of Biomedical Engineering*, Vol. 39, No. 7, July 1992, pp. 752–756, refers to passing linearly-polarized light through the anterior chamber of an excised human eye and determining the glucose level of the aqueous eye humor based on the phase shift between the reference signal and the measurement signal that was affected by glucose. A helium-neon laser beam, coupled through a rotating linear polarizer along with two stationary linear polarizers and two detectors, is used to produce reference and measurement signal outputs. The amplitudes of these outputs varied sinusoidally with a frequency twice that of the angular velocity of the rotating polarizer. The phase difference of the outputs would be proportional to the polarization rotation introduced in the measurement beam by the anterior chamber of the eye.

Due to problems with both types of systems there is a continuing need for improved non-invasive analytical instruments and methods that would provide essentially the same accuracy as conventional invasive blood glucose tests. There also is a need for non-invasive, low-cost methods and instruments for the measurement of glucose levels in diabetic patients. There also is a need for a durable, cost-effective, and environmentally conscious nondisposable apparatus for measuring blood glucose. In view of such the present invention now provides an apparatus for non-invasive measurement of blood glucose concentration.

SUMMARY OF THE INVENTION

A human subject is presented with a changing light stimulus or pattern in which one or several parameters, for example the luminance, color, flicker frequency, spatial contrast, speed, etc., of a portion of the pattern or of the whole of the pattern, gradually change in a manner which stimulates a first retinal system (e.g., the P-system) and a second retinal system (e.g., the M-system) in a continuously changing ratio. The stimulus or pattern is observed until the person observing the pattern subjectively notes a specific change in the appearance of the light pattern, for example the appearance of a specific color in the light pattern, or the reversal in the direction of rotation of the light pattern. The specific change is associated with a specific ratio of stimulation of the M- and P-systems, for example the point of balanced stimulation of the two systems, or M-P crossover point. The value of at least one of the variable light stimulus parameters at the moment of occurrence of the specific change in appearance of the light stimulus, can be calibrated to the subject's blood glucose level via prior measurements of the subject's blood glucose level. Such value of the variable stimulus parameter when the specific change in the stimulus appearance occurs, will shift for any given person as the glucose level of the person changes, because the sensitivity of the two retinal systems change relative to each other in response to changes in blood glucose level.

In one preferred embodiment, a series of images resembling windmill wheels are presented to a person in a manner which causes the person to perceive rotation of the wheel. A gradual change in the brightness or color of portions of the images or their background is then effected in such a manner that the series of images stimulates one retinal system (M or P) over time at a certain rate, and the other retinal system (P or M) at a different rate. The different manner in which the M- and P-systems respond to changes in the parameters of a light pattern make it possible to stimulate the M- and P-systems at different rates by varying continuously one or several parameters in the light pattern. The resultant ratio of stimulation of the two systems changes gradually over time. This gradual change in the ratio of stimulation of the two retinal systems is continued until the patient notes a reversal in the direction of apparent rotation of the wheel—rotation reversal indicating a balanced stimulation of the M- and P-systems, or M-P crossover point. A change in blood glucose level affects the retinal systems in a manner which causes the M-P crossover point to shift in a predictable and consistent manner, because the sensitivity of each of the two retinal systems is affected differently relative to each other by changing blood glucose levels. The value of the variable parameter or parameters of the light stimulus at the point when the person notices the rotation reversal is directly related to blood glucose levels. Thus, by relying on the differential response of the M-system and the P-system to changes in certain types of light patterns, and on the differential change in sensitivity of the M-system and the P-system with blood glucose levels, the device and method provide an accurate, convenient, non-invasive means of measuring a patient's blood glucose level.

An object of the invention is to provide a non-invasive optical means of determining a patient's blood glucose level.

Another object is to provide the non-invasive means for determining glucose levels by using images or light patterns which provide visual stimulation to the retina and determining with such images or light patterns changes that take place in a patient's retina in response to changes in blood glucose levels.

Another object of the invention is to provide a device which creates a changing light stimulus which when observed reaches an M-P crossover point which is related to the blood glucose level of the observer.

Another object is to provide such a device which gradually stimulates one retinal system more and more and another retinal system less and less and provides for an actuation means which upon actuation records a point which can be related to the relative stimulation of each system which information can be related to the blood glucose level of the patient.

Yet another object of the invention is to provide a device which provides a light stimulus with an observable M-P crossover point which device is calibrated with an established relationship between known blood glucose levels and measured M-P crossover points.

A feature of the invention is that it uses changing light patterns.

An advantage of the invention is that it is a non-invasive method of determining a blood glucose level.

Another feature of the invention is that it capitalizes on the different sensitivities of the M-system and the P-system to determine information on blood glucose level.

Another advantage is that the method can be quickly carried out in only a few seconds.

Another advantage is that the device for measuring glucose levels via optical means can be inexpensively manufactured.

Another advantage of the device of the invention is that the patient can reuse the device a plurality of times, i.e., it is not a one use disposable item and does require the use of any disposable components.

Still another advantage is that the device is small (less than 10 cm in any dimension) light weight (less than 0.5 kg) and thus may be conveniently carried and used by an individual on an out-patient basis.

These and other objects, advantages and features of the present invention will become apparent to those persons skilled in the art upon reading the details of the structure, methodology and usage as more fully set forth below with reference being made to the accompanying figures forming a part hereof.

BRIEF DESCRIPTION OF THE DRAWINGS

FIG. 17 is a graph demonstrating how reaction time is compensated for.

DETAILED DESCRIPTION OF THE INVENTION

Figure 1:
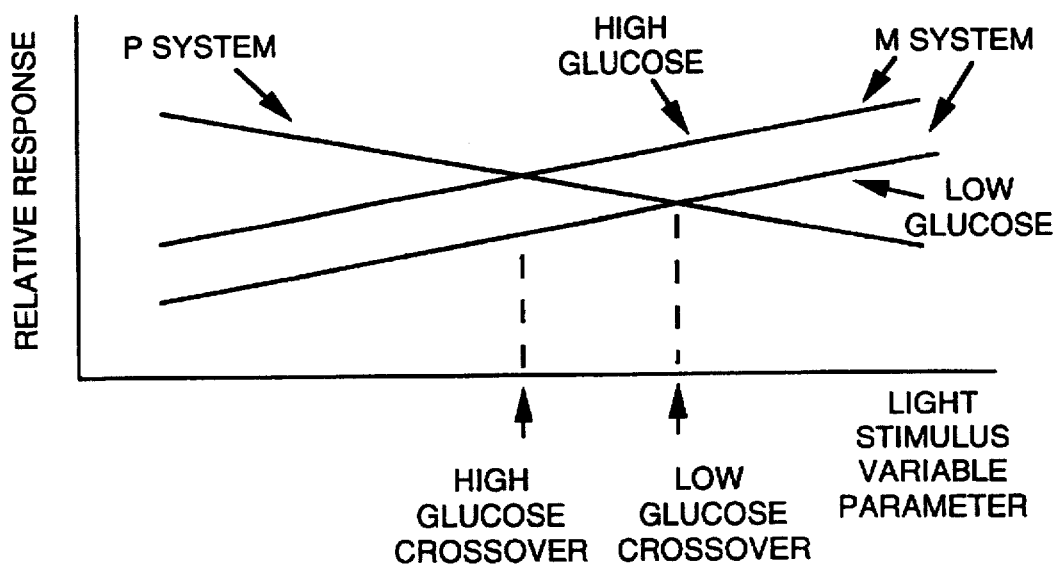
FIG. 1 is a graph which conceptually shows the relative sensitivities of the M- and P-retinal systems at different glucose levels.

Before the present optical method and device for determining blood glucose levels is described, it is to be understood that this invention is not limited to the particular process steps, light changing, light stimulus or other steps and components described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural reference unless the context clearly dictates. Thus, for example, reference to "a changing light stimulus" refers to one or more changing light stimuli, reference to "an actuation means" refers to one or more means and so forth.

Unless defined otherwise all technical and scientific terms used herein have the same meaning as commonly understood by one of ordinary skill in art to which this invention belongs. Although methods and materials similar or equivalent to those described herein can be used in the practice or testing of the present invention, the preferred methods and materials are now described. All publications mentioned hereunder are incorporated herein by reference.

The publications discussed herein are provided solely for their disclosure prior to the filing date of the present application. Nothing herein is to be construed as an admission that the invention claimed herein is not entitled to antedate such publications by virtue of prior invention.

Definitions

The term "appearance of colors" is used to describe a subjective visual effect occurring at a specific frequency when the retina is stimulated with a flickered light of variable frequency. For example, the appearance of colors can consist of pink and green irregular patches that appear to radiate from the point of fixation.

The term "cessation of radial movement" is used to describe a subjective visual effect occurring at a specific frequency when the retina is stimulated with a flickered light of variable frequency. For example, at lower frequencies, faint shadows like concentric ripples in water radiate from the point of fixation towards the periphery, while at higher frequencies, the shadows travel in the opposite direction. At an intermediate frequency, the radial movement of the shadows ceases momentarily before changing direction; this is the frequency of cessation of radial movement and is an example of a subjective visual effect occurring during the observation of a changing light pattern.

The term "changing light pattern" is intended to mean a light pattern that changes over time with respect to one or several of its defining parameters, for example its luminance, color, shape, size or rate of flicker.

The term "changing parameter" shall mean any parameter that changes during the presentation of a light pattern, in order to provide a changing stimulation to the observer's retina. For example, a changing parameter in the windmill light pattern may be the luminance of the background, which could increase gradually. In a flickered stimulus, the flicker frequency may increase, or the length of the ON periods may increase over time.

The term "continuously increasing ratio" is used to describe the ratio of stimulation of one retinal system over the other, when such ratio increases continuously. Thus, if the sensitivity of the M- and P-systems change as shown in FIG. 1, and if the light stimulus is assumed to change from left to right along the horizontal axis, the ratio of M to P stimulation in FIG. 1 increases continuously from left to right, starting with a value of less than 1 on the left end of the diagram, reaching a value of 1 at the M-P crossover point, and continuing to increase to values greater than 1 towards the right side of the diagram.

The term "critical parameter value" is used to describe the value of a variable parameter in a changing light pattern, at the point when the subject notices the subjective visual effect.

The term "grid pattern" is used to describe a subjective visual effect occurring at a specific frequency when the retina is stimulated with a flickered light of variable frequency. The effect consists of a regular pattern, which some observers describe as a fine square grid, and others as a fine honeycomb pattern.

The terms "light pattern", "light stimulus" and the like are used interchangeably herein and are intended to mean any arrangement of light-emitting surfaces that can be used to stimulate the retina. A light pattern can be specified by three kinds of properties: spectral properties (the color of each component part), spatial properties (the size, shape and location of each part), and temporal properties (how each part changes with time). Examples of light patterns are a flickering light or a sequence of windmill images that appear to rotate. A light pattern can be produced with a variety of light sources, such as a CRT screen, an LCD screen, LEDs, fluorescent or incandescent sources, arc or gas discharge lamps, flash tubes, or natural sun light. In order to stimulate the retina with a light pattern the observer may look at the actual light source or the observer may look at an object that in itself is not light-emitting, but receives the light from a light source and re-directs this light to the eye of the observer by either reflection, scatter, diffusion or refraction. Appropriate filters and time-control devices can be used to give the desired spectral and temporal properties to the light pattern.

The term "light pattern parameters" is intended to mean the set of parameters that define a light pattern at one moment in time. Light pattern parameters define the light pattern along three dimensions: spectral parameters, spatial parameters and temporal parameters. Examples of light pattern parameters are color, luminance, size, and rate of flicker.

The term "luminance" shall mean the quantitative measure of brightness of a light source or an illuminated surface, formally defined as luminous flux per unit solid angle emitted per unit projected area of surface.

The terms "M-retinal system", "M-system", "P-retinal system" and "P-system" are used herein to describe the two complementary components of the visual system, presently regarded in vision science as the main channels for processing visual information. The M- and P-retinal systems originate at the ganglion cell layer of the retina and connect respectively to the magnocellular and parvocellular layers of the lateral geniculate nucleus in the brain. The M- and P-systems differ in their color selectivity, contrast sensitivity, temporal properties, spatial resolution and sensitivity to changes in blood glucose levels. The two systems are compared in Tables 1 and 2. It is understood that the differences with respect to some parameters may be gradual even though Tables 1 and 2 appear to imply a discrete and complete separation of sensitivities. The present invention makes use of the differences in the M- and P-systems to stimulate the two systems selectively and to gradually shift the stimulation from predominantly M to predominantly P or vice versa.

The terms "M-P crossover point", "crossover point" and the like are used interchangeably herein to define the point where the M- and P-systems are stimulated substantially equally. The M-P crossover point can be reached by changing the light pattern gradually in such a manner that the light pattern first stimulates one system more than the other and then gradually changes the relative stimulation of the systems until both systems are stimulated substantially equally. When the crossover point is reached the two systems perceptual conveying perceptual information about the stimulus, a point that is often accompanied by the appearance of a subjective visual effect. The subjective visual effect results from the sudden change of channel that carries the dominant information regarding the visual stimulus. Away from the crossover point, the system that receives greater stimulation dominates the perception of the stimulus. The M-P crossover point is used in this invention to measure changes in sensitivity of the M system, which are caused by shifts in blood glucose levels. Changes in M system sensitivity translate into shifts in the M-P crossover point, as explained conceptually in FIG. 1. Thus by measuring shifts in the M-P crossover point, one can indirectly measure changes in sensitivity of the M system and thus changes in blood glucose levels.

The term "perceived characteristic" is used to describe a subjectively perceived property or quality in a light stimulus or pattern, such as the perception of colors in a light flickering at a certain constant frequency near 25 Hz, or the perception of apparent rotation in a sequence of images resembling a windmill pattern with constant color, luminance and background. The perceived characteristic arises from the simultaneous stimulation of several retinal mechanisms that have different sensitivity to the light stimulus, which results in competition or interference between the mechanisms involved. The term perceived characteristic is used for a perceived quality in a light pattern that is not changing over time, whereas the term subjective visual effect, defined below, is used for a perceived quality in a light pattern that is changing over time.

The term "ratio of stimulation of M and P systems" is used to describe the amount of stimulation of one retinal system relative to the other, or equivalently the ratio between the degree of stimulation of one system and the degree of stimulation of the other. When a light stimulus changes gradually, it may first stimulate preferentially the M-system, while stimulating the P-system only a small amount. As the stimulus changes, it may stimulate the M-system less and less and the P-system more and more, in which case we say that the ratio of M-system stimulation over P-system stimulation is decreasing. This case is illustrated in FIG. 1. However, the ratio of stimulation can also decrease in a variety of other ways, for example if the M-system is stimulated less and less while the P-system is stimulated in a constant amount, or also less and less but at a slower rate of change than the rate at which the stimulation of the M-system is changing.

The term "retinal system" is used to describe any of the functional components of the visual system, which components are distinguished from each other by their differential sensitivity to light stimuli. Vision scientists assume that the visual system in higher mammals is organized as a group of parallel systems, each containing neurons that have distinctive physiological properties and which analyze different aspects of the retinal image. These systems, also called pathways, channels, or mechanisms are organized as complementary pairs e.g., cone and rod, ON and OFF, X and Y, chromatic and achromatic, pattern and movement, sustained and transient, tonic and phasic, M and P. Some of these system pairs overlap—for example, the tonic and phasic pair of systems seem to correspond to the X and Y pair, to the P and M pair and to the chromatic and achromatic pair. The segregation of visual processing into pairs of systems starts at the retina and continues into the lateral geniculate nucleus and higher visual centers of the brain.

The term "subjective visual effect" refers to a sudden and dramatic change in the perceived quality of a gradually changing light pattern, or the sudden appearance of a quality or characteristic in the light pattern that was not present before. An example is the appearance of patches of color at a specific flicker frequency, when the light stimulus is a uniform white surface illuminated with a white light flickering at increasing frequency and observed through a red filter. Another example is the sudden reversal in the perceived direction of rotation of a sequence of windmill images in which the luminance of a set of vanes changes gradually. The changing parameter in these examples changes at such a slow rate that the observer does not perceive the parameter change in itself. The sudden change in perceived quality is a dramatic discontinuity in the appearance of the light pattern and is indicative of a new mechanism taking over the perception of the stimulus.

The term "visual system" is used to describe the post-optical, or neural portion of the human visual system. In this definition, the visual system starts at the retina and includes the visual centers of the brain, but does not include the optical portions of the eye, such as the cornea, aqueous humor, crystalline lens or vitreous humor.

Method and Device in General

The device of the invention is preferably a hand-held, portable, light weight (less than 0.5 kg) device comprised of a body member having positioned thereon a means for generating a changing light pattern. The light pattern stimulates the retina by virtue of the subject looking at the light pattern. Preferably, the light pattern is projected on a specific area of the retina, and preferably this area is to remain substantially constant throughout the measurement. Thus a fixation target, consisting of a point, a cross or any such similar visible target is provided within the light pattern, in order to direct the line of sight of the subject during the measurement and thus define the retinal area stimulated by the light pattern.

The light pattern is preferably a light pattern which changes over time. More specifically, either the entire light pattern or a part of the light pattern changes over time with respect to one or more different parameters. For example, the parameters may be selected from the group consisting of color, luminance level, contrast, shape, size, detail content, texture, speed of movement, direction of movement and rate of flicker. In particular situations it is desirable to use different combinations of variable parameters in order to make the perceived effect of the M-P crossover point more dramatic.

The light pattern must stimulate the retina in a specific manner. Specifically, the light pattern should be designed to stimulate two retinal systems wherein the sensitivity of one system changes with glucose levels substantially more than the sensitivity of the other retinal system. Thus, it is desirable to provide a light pattern which stimulates the M- and P-systems of the retina and to stimulate these systems in a changing ratio. Preferably, the M- and P-systems of the retina are continuously and gradually stimulated in an increasing ratio, e.g., the M-system is continuously and gradually stimulated more relative to the P-system.

The stimulation of the retinal systems by the light pattern continues until the patient perceives a subjective visual effect in which the light pattern appears to undergo a radical change in appearance or to suddenly acquire a quality that was not present before. The subjective visual effect may be virtually any perceivable change in the light pattern and generally consists of a change such as the appearance of color patches, the appearance of a grid pattern, or the perception of radial movement stopping, starting, or reversing direction. It should be noted that such visual effects are perceived effects in that the color patches or the grid pattern were not present in the stimulus at all, but the stimulus was a uniform, featureless field of a constant color. Another subjective visual effect which might be noted is the reversal in the direction of rotation of a light pattern. This pattern may not be rotating at all but rather presenting a series of images that creates the impression or appearance of rotation. That apparent rotation may then reverse direction and the light pattern may then appear to rotate in the opposite direction when the stimulation passes over the M-P crossover point, as will be explained in greater detail in the Example 2 section.

Figure 2:
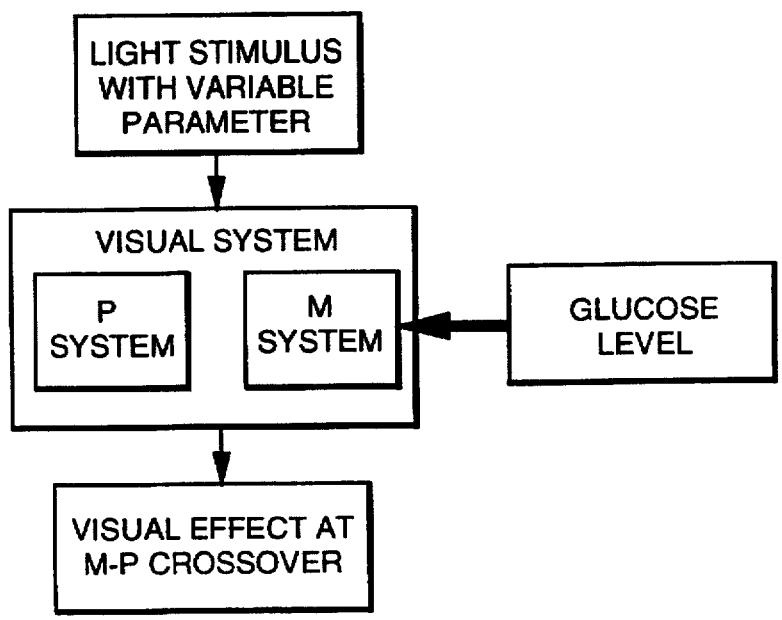
FIG. 2 is a schematic block diagram of an aspect of the invention.
Figure 3:
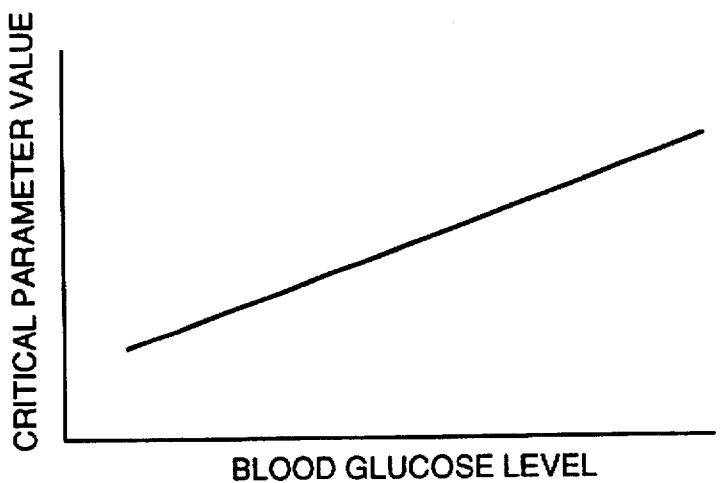
FIG. 3 is a graph which conceptually shows how the M-P crossover point changes as blood glucose level changes.

A block diagram of the basic principles of the present invention is shown in FIG. 2. Specifically, FIG. 2 shows that a light stimulus is provided which light stimulus provides a variable parameter, e.g., a continually increasing rate of light flicker. This light stimulus is presented to the visual system which includes the P-system and the M-system. The M-system is affected by glucose levels substantially more than the P-system. The subjective visual effect determines that the crossover point has been reached and this allows the value of the variable parameter at crossover to be measured. By relating the variable parameter values at crossover with glucose levels measured by conventional means the device can be calibrated. A relationship is established between the M-P crossover value and the blood glucose level as is shown within FIG. 3. The diagram shown within FIG. 3 is shown only for illustration purposes, and it does not imply that the relationship follows a straight line. Clinical tests will determine the actual characteristic of this relationship. When the patient activates the device indicating that the crossover point has occurred the microprocessor relates the parameters defining the light stimulus at that moment to the corresponding blood glucose level previously stored, thereby providing the patient with information on current glucose levels in a non-invasive manner.

Physiological Basis

The operability of the device and method of the present invention is not dependent on the following explanation with respect to how the invention works. However, the following information is given in order to provide those skilled in the art with an explanation on how the invention works i.e., the underlying physiological events which make it possible for the device and method to determine glucose levels in the blood which enters the retina. The explanation is based on currently available theories and knowledge about the operation of the retina and the visual system. However, these theories and knowledge may change over time without affecting the operability of the device and method of the present invention.

It is well understood that glucose is present in blood and can migrate to all tissues via the circulatory system. In particular glucose is an important metabolite for the retina. The retina possesses a high rate of metabolic and electrical activity which is almost exclusively fueled via the oxidative breakdown of glucose (Noell, W. K. 1959, The Visual Cell: "Electric and Metabolic Manifestation of its Life Processes," Am. J. Physiol. 48:347; Winkler, B. S. 1975, "Dependence of Rat and Rabbit Photoreceptor Potentials Upon Metabolism in vitro," Exp. Eye Res. 21:545). The retina obtains the required glucose from an abundant blood supply provided to the retina via the choroid capillaries. Not only does the retina utilize glucose for its metabolic and electrical activity, but the retina is able to consume glucose in proportion to the amount of glucose available over a wide range of glucose levels (Ames IIIA., and Gurian, B. S. 1963, "Effects of Glucose and Oxygen Deprivation on Function of Isolated Mammalian Retina," J. Neurophysiol. 26:617; Winkler, B. S. 1972, "The Electroretinogram of the Isolated Rat Retina," Vision Res. 12:1183; Winkler, B. S. 1981 "Glycolytic and Oxidative Metabolism in Relation to retinal Function," J. Gen. Physiol. 77:667).

In view of the above it can be anticipated that changes in the blood glucose concentration will have noticeable effects on the visual system. Such effects have been demonstrated by others in areas unrelated to the subject of this invention. Specifically, glucose concentration affects rod-mediated responses in the perfused cat eye (Macaluso, C., Onoe, S. and Niemeyer, G. 1991, "Discrete Changes in Glucose Level Affect Rod- but not Cone-function in the Perfused Cat Eye," Invest. Ophthalmol. & Visual Science, Supplement 32:903); high blood glucose concentration decreases the detection thresholds with respect to low-contrast gratings and increases the ERG amplitude in humans (Barlow, R. B. Jr., Boudreau, E. A. and Pelli, D. G. 1993, "Metabolic Modulation of Human Visual Sensitivity, " Invest. Ophthalmol. & Visual Science, Supplement 34:785); and lastly, low blood glucose concentrations increase dark-adapted detection thresholds in humans (McFarland, R. A. and Forbes, W. H. 1940, "The Effects of Variations in the Concentration of Oxygen and of Glucose on Dark Adaptation," J. Gen. Physiol. 24:69).

The above evidence demonstrates that the ability of an individual to perceive certain types of images changes with fluctuations in blood glucose level. Based on this it can be understood that the appearance of some images can change with changes in blood glucose level. The present invention utilizes this basic principle to provide a methodology and a device which calculates blood glucose levels based on changes in the appearance of a specially designed visual stimulus. The mechanism of operation of the invention can be explained on the basis of the M- and P-retinal systems, a subject that is introduced next.

The visual function of the human retina is mediated largely by two complementary systems referred to as the M-system and the P-system. This terminology is currently used by those skilled in the art and for purposes of the invention other terms could be used provided the terms refer to two retinal systems which are sensitive to different information components of the light stimulus as listed in Table 1 below. The M-system is evolutionary older and specializes in colorless detection of moving objects. The M-system provides information about the prevailing luminance level and the presence and movement of approaching objects. The P-system evolved in vertebrates and is particularly well developed in mammals. The P-system specializes in finding detail in an image in order to facilitate recognition of the object from which the light stimulus is received.

The following Table 1 provides a comparison of the M-system and the P-system in terms of their relative sensitivities. The information is given in terms of "High" and "Low" parameters. For example, Table 1 indicates that the sensitivity of the M-system to fast flicker is high, whereas the sensitivity of the P-system is low. It will be understood by those skilled in the art that both systems have some degree of sensitivity with respect to the various stimulus within Table 1. However, the "High/Low" readings given are intended to show which system is preferentially sensitive to the stimulus listed. This is done to emphasize differences in that the present invention is based on the different sensitivities of the two systems.

TABLE 1

RETINAL M- AND P-SYSTEMS COMPARED

|  | M | P |
| --- | --- | --- |
| Sensitivity to blood glucose levels | High | Low |
| Sensitivity to fast flicker | High | Low |
| Sensitivity at low light levels | High | Low |
| Sensitivity to low-contrast patterns | High | Low |
| Sensitivity to steady light | Low | High |
| Sensitivity to color | Low | High |
| Sensitivity to fine detail | Low | High |
| Sensitivity to high-contrast patterns | Low | High |

Additional parameters which can be used to distinguish the M-system from the P-system are provided below in Table 2.

TABLE 2

| Evolutionary age | Old | New |
| --- | --- | --- |
| Conduction velocity | Fast | Slow |
| Spatial integration | Large | Small |
| Cell size | Large | Small |

Fluctuations in glucose level affect visual function in general and in particular by having a greater effect on the sensitivity of the M-system with no or a substantially smaller effect on the P-system. This conclusion has been reached via experimental results shown herein, which are discussed in detail in the Example 1 and Example 2 sections and summarized in FIGS. 6–10. Such experimental results are consistent with the work of others cited earlier in this section who have reported an effect of glucose levels on visual function. Specifically, Macaluso et al. (Macaluso C., Onoe S. and Niemeyer G. 1991, "Discrete Changes in Glucose Level Affect Rod- but not Cone-function in the Perfused Cat Eye, " *Invest Ophthalmol & Visual Science, Supplement* 32:903), found that the rod responses are affected by changes in glucose concentration, whereas cone responses are not. Similarly in humans, McFarland et al., (McFarland, R. A. and Forbes, W. H. 1940, "The Effects of Variations in the Concentration of Oxygen and of Glucose on Dark Adaptation," *J. Gen. Physiol.* 24:69) found that that the sensitivity of rod vision, but not that of cone vision, changes with variations in glucose level. It is known through the work of others that rod responses are carried only or primarily by the M-system, whereas the P-system carries only or primarily cone responses (Purpura K., Kaplan E., Shapley R. M. 1988, Background Light and the Contrast Gain of Primate P- and M-Retinal Ganglion Cells, *Proc. Natl. Acad. Sci. USA* 85:4534). Thus, even though neither Macaluso et al. nor McFarland et al. mention any connection between their results and the M- and P-systems, their results are consistent with the conclusion that changes in glucose level affect the sensitivity of the M-system and not that of the P-system, and furthermore, that the direction of this effect is such that higher glucose levels cause an increased sensitivity in the M-system. Additional support for this conclusion comes from the work of Barlow et al, also cited earlier in connection with glucose levels affecting visual function (Barlow, R. B. Jr., Boudreau, E. A. and Pelli, D. G. 1993, "Metabolic Modulation of Human Visual Sensitivity," *Invest. Ophthalmol. & Visual Science, Supplement* 34:785). These authors found that higher glucose levels increase the ability of human observers to detect low contrast patterns. Again, these authors did not connect this finding with the M- or P-systems, but it is known from the work of others that patterns of low contrast are preferentially detected by the M-system (Shapley, R. 1990, "Visual Sensitivity and Parallel Retinocortical Channels, " *Annu. Rev. Psychol* 41:635–58). Thus the results of Barlow et al are also consistent with the conclusion that increases in glucose level affect preferentially the M-system relative to the P-system by raising the sensitivity of the M-system. In summary, the experiments reported later in this patent and summarized in FIGS. 6–10, show that increases in blood glucose level raise the sensitivity of the M-system more than that of the P-system. This conclusion, although not stated explicitly in any prior report, receives support from the above cited reports, when one interprets those reports in terms of known properties of the M- and P-systems. This conclusion is an important part of the physiological explanation of how the present invention operates. To further explain the physiological basis of the present invention we next state some additional properties of the M- and P-systems.

The M-system and the P-system have complementary specializations. More specifically they respond inversely to several parameters of a light stimulus as indicated in Table 1. For example the M-system is insensitive to color and most sensitive to fast flicker as well as coarse and low-contrast patterns while operating at low light levels. However, the P-system is sensitive to color and most sensitive to slow flicker and to patterns with fine detail and high contrast while functioning best at high light levels (Kaplan, E., et al. 1988, "Color and Luminace Contrast as Tools for Probing the Primate Retina," *Neuroscience Res. Suppl.*8: S151; Schiller, P. H. and Logothetis, N. K. 1990, "The Color-opponent and Broad-band Channels of the Primate Visual System," *Trends in Neurosciences* 13:392; Kaplan, E., Lee, B. B. and Shapley, R. M. (1990) "New Views of Primate Retinal Function," In *Progress in Retinal Research*, N. N. Osborne and G. J. Chader, editors. Pergamon Press, Oxford, pp 275–330). As explained below, this complementary specialization of the M- and P-systems along with the selective effect of glucose levels on the M-system sensitivity are two facts that help explain how the present invention derives blood glucose information from the subjective response to a light stimulus.

Determining Glucose Levels

The complementary nature of the sensitivity of the M- and P-systems to light stimuli makes it possible to design a changing light stimulus or pattern that stimulates the two systems in sequence, in other words, a light stimulus or pattern that first stimulates preferentially the M-system and later the P-system, or vice versa. This is accomplished by varying continuously a light pattern parameter that elicits complementary or contrary responses in the M- and P-systems. The variable parameter in the light pattern can be any of a variety of different parameters. For example, it is possible to continually and gradually change one or more parts of a light stimulus or pattern with respect to their color, luminance level, contrast, shape, size, detail content, texture, speed of movement, direction of movement including rotation, or rate of flicker. For example, light flickered at low frequency (e.g., 10 Hz) stimulates the P-system to a large extent and the M-system to a small extent. As the frequency increases, the flickered light stimulates the P-system less and less and the M-system more and more, until at high frequency (e.g., 40 Hz), the flickered light stimulates predominantly the M-system. In this example the variable frequency of the flickered light is a variable parameter in the changing light pattern. Near the middle of this range of frequencies (near 20-25 Hz), the sweep of flicker frequencies passes through a point—the M-P crossover point—where the M- and the P-systems are stimulated about equally.

The term M-P crossover point denotes a theoretical point of balanced stimulation of the M- and P-systems, and since it is not possible to measure objectively the degree of stimulation of the M- and P-systems in a human observer, the M-P crossover point cannot be determined objectively. However, it can be measured subjectively, thanks to the fact that the crossing of the M-P crossover point is frequently accompanied by a sudden and dramatic change in appearance of the light stimulus—a subjective visual effect. This visual effect results from the shift in perceptive channels of the light pattern from M-system dominated to P-system dominated or vice versa. The subjective visual effect noticed by an observer depends on the specific design of the light pattern and the parameter that is made to change. Thus for example in the flickered light stimulus described above, a subjective visual effect consists of the sudden appearance of colored patches. Another subjective visual effect associated with the flickered light and perceived at a slightly different flicker frequency is the appearance of a grid or fine geometric pattern, which for some observers is a regular square grid and for others a honeycomb pattern. Yet another subjective visual effect associated with the flickered light is the cessation of the radial movement of subtle shadows, which shadows appear to move away from the center of the illuminated field at lower flicker frequencies, and in the opposite direction at higher flicker frequencies. These three visual effects, the color patches, the grid pattern, and the stopping of the radial movement of subtle shadows, occur at slightly different flicker frequencies in the 20-25 Hz range. More than one subjective visual effect is associated with the flickered light stimulus presumably because the M-P crossover for each light stimulus attribute—color, fine detail, movement—occurs at slightly different flicker frequency values. A different type of light pattern is described in the section Example 2, a pattern consisting of an apparently-rotating windmill pattern. This type of light pattern has a very clear subjective visual effect associated with the M-P crossover point, which effect consists of a reversal in the direction of apparent rotation of the windmill pattern.

The relative sensitivity of the M-system and P-system to a hypothetical variable parameter (e.g., changing frequency of the light flicker) is shown in FIG. 1. As indicated in FIG. 1 the sensitivity or relative response of the P-system is high when the variable parameter has a low value, which is indicated in FIG. 1 as being on the left extreme of the horizontal scale. As the variable parameter increases the relative response or sensitivity of the P-system decreases. However, the opposite occurs with the M-system. Specifically, the relative response or sensitivity of the M-system is low when the variable parameter has a low value. The sensitivity or relative response of the M-system increases as the value of the variable parameter increases. The point at which the M- and P-systems are stimulated equally is referred to as the crossover point. As shown within FIG. 1, there are different and distinct crossover points depending on the glucose level. Since an increase in blood glucose level raises the sensitivity of the M-system, a plurality of crossover points exists for the same subject, each crossover point corresponding to one glucose level. FIG. 1 shows two different glucose levels thus two different crossover points. Thus, the crossover point will occur at different values of the variable parameter for the same patient if the patient has different glucose levels. Since the subjective visual effect is associated with the crossover point, the subjective visual effect will occur at different values of the variable parameter for the same patient if the patient's glucose level changes. Therefore, determining the point relative to the variable parameter scale where the subjective visual effect occurs can be used to determine blood glucose levels, once a known relationship has been established between variable parameter values when the subjective visual effect is noted, and corresponding blood glucose levels. This relationship can be established during calibration of the device, a topic which is discussed in the next section.

It should be noted that the present invention can also be implemented as a single-point device—a device which does not provide a blood glucose value, but indicates if the blood glucose level is above or below certain value. This information is valuable for some individuals who, for example, wish to maintain their blood glucose concentration below a certain level, for example below 200 mg/dL, and who do not need to know what the exact level is. The single-point device is a simpler device in that it uses a constant light pattern, as opposed to a changing light pattern, does not require patient's input, does not need to perform any calculations or checks and does not need to store look-up tables. The device can be calibrated so that the light pattern has one appearance when the blood glucose level is above 200 mg/dL and a different appearance when the blood glucose level drops below this discrimination point. For example, the light pattern can consist of an apparently-rotating windmill or wheel pattern. The parameters of the pattern—color and luminance of the vanes, frame rate, background luminance, etc.—can be chosen so that for a specific individual the pattern appears to rotate in one direction when the individual's blood glucose level is above 200 mg/dL and in the opposite direction when the individual's blood glucose level drops below that value. To understand how a single-point device works using the present invention, reference is made to FIG. 1, wherein two crossover points are shown: one labeled "high glucose crossover," and the other "low glucose crossover." As explained earlier, each crossover point represents the point when the changing light pattern changes appearance, and this point moves to a new value of the light stimulus parameter when the observer's blood glucose level changes. Now suppose that the light pattern parameter is fixed and that it has a value between the points identified as high glucose crossover and low glucose crossover. As can be seen from the diagram within FIG. 1, when blood glucose is high, the sensitivity of the M-system rises and the perception of the fixed pattern is dominated by the M-system, whereas when the blood glucose is low, the sensitivity of the M-system is low and the perception of the light pattern is dominated by the P-system. The device can be calibrated so that the change in appearance corresponds to a desired discrimination point in the glucose scale, for example 200 mg/dL. Thereafter, as the blood glucose level of the individual rises above or falls below the discrimination level for which the device has been calibrated, the appearance of the light pattern changes, and this change in appearance can be used to determine whether the individual's blood glucose level is above or below the discrimination level.

The following explanation is provided to further clarify the concept of crossover point and subjective visual effect. When a human subject is involved in normal observation of objects in every day life subjective visual effects at crossover points are not generally recognized in that the individual is generally viewing complex visual scenes. Within such complex scenes visual stimulus parameters change all the time, and crossover values are reached frequently, however the observer does not ordinarily observe subjective manifestations of crossover points. This is because a complex visual scene contains a multitude of stimulus parameters that simulate the retinal M- and P-systems simultaneously and in a large number of retinal locations. The M- and P-systems thus convey to the central nervous system largely redundant information—redundancy that helps create a congruent visual experience. This visual experience is not altered significantly by the change of a single or a few visual stimulus parameters. However, an artificial stimulus or pattern may contain few stimulus parameters, all of which may be arbitrarily manipulated to create an unusual visual experience. The visual experience can then change drastically and suddenly in response to a small change in the stimulus parameters as the information reaching the central nervous system changes from M-dominated to P-dominated or vice versa.

The theory presented in this section about the M-P crossover point has been advanced as a plausible mechanism which is consistent with existing knowledge and which explains satisfactorily the operation of the present invention. However, the validity of the theory is not necessary for the operability and usefulness of the device and method of the present invention. In particular, it is not necessary that the subjective visual effect occur exactly at the M-P crossover point. The present method and device would operate as well if the subjective visual effect occurs at any point in the scale of the variable parameter, as long as the point where the visual effect occurs shifts along the scale of parameter values in a consistent and predictable manner when blood glucose levels change.

Calibration

In order to calibrate a device of the invention it is necessary to establish the relationship between parameter values at the point where the subjective visual effect is noted ("critical parameter values") and the values of blood glucose concentration that correspond to those points ("corresponding glucose values" or "corresponding blood glucose values"). An example of such a relationship is shown schematically in the graph within FIG. 3, wherein the vertical axis of the graph corresponds to critical parameter values and the horizontal axis represents corresponding glucose values. A simple linear relationship has been assumed in this diagram for illustration purposes.

The relationship between critical parameter values and corresponding glucose values is established by measuring simultaneously or in close time proximity pairs of values, one critical parameter value and its corresponding glucose value. Specifically, the patient views the changing light pattern in which the variable parameter is gradually changing over time. This gradual change is maintained until the patient notes the subjective visual effect associated with the crossover point. At this point the value of the variable parameter, or critical parameter value is noted, preferably by way of the patient actuating an actuation means such as a key or a button in the device, which actuation prompts the device to record internally the value of the variable parameter at that moment. Simultaneously or substantially contemporaneously with the variable parameter measurement, the blood glucose level of the patient is determined by any conventional means and entered into the memory of the device. Thus the measurement yields two numbers, the critical parameter value and the corresponding blood glucose level, which are stored into the memory of the device. This process of calibration is repeated several times when the patient's glucose level would be expected to be different. Preferably, readings are taken at very low and very high levels as well as a number of evenly spaced levels therebetween. Thus, pairs of numbers are stored in the memory of the device, each pair consisting of a critical parameter value and a corresponding blood glucose value. The number of pairs of values needed for a full calibration of the device depends on the shape of the graph that relates parameter values and glucose values, the constancy of this graph from one patient to another, and the accuracy desired in the measurements. The greater the regularity of the graph and the greater the constancy of the graph among patients, the fewer the number of calibration points required for a given degree of desired measurement accuracy. The shape of the graph and its degree of constancy among patients can be determined in clinical tests.

After completing these calibration steps the patient can, thereafter, determine his or her glucose level by viewing the light stimulus and noting the moment when the subjective visual effect is detected. When the subjective visual effect is noted the patient actuates a means for noting such and the actuation of such prompts the device to record the parameter value at that moment. The glucose value that corresponds to the recorded parameter value is then looked up in the table of stored pairs of values, if an exhaustive list has been stored. If an exhaustive list of all possible parameter values has not been stored in memory, the glucose value that corresponds to the recorded parameter value will be calculated by a well known interpolation technique. This technique consists of looking up from memory the stored parameter values that are closest to the recorded parameter value, one greater and one smaller than the recorded parameter value, and assuming a certain relationship, for example a linear relationship, between glucose values and parameter values in the range between such two stored parameter values.

Preferably, several determinations of critical parameter values are performed consecutively and automatically by the device, sometimes while the parameter values increase, and sometimes while the parameter values decrease. Several determinations are performed in order to increase the accuracy of the measurement, to remove the effect of reaction time, and to check the consistency of the patient's input, as is further explained in the section Measuring Sequence. In order to insure accuracy the calibration of the device can be repeated periodically e.g., weekly, monthly, quarterly, or yearly as needed.

Hand-held Device

Figure 14:
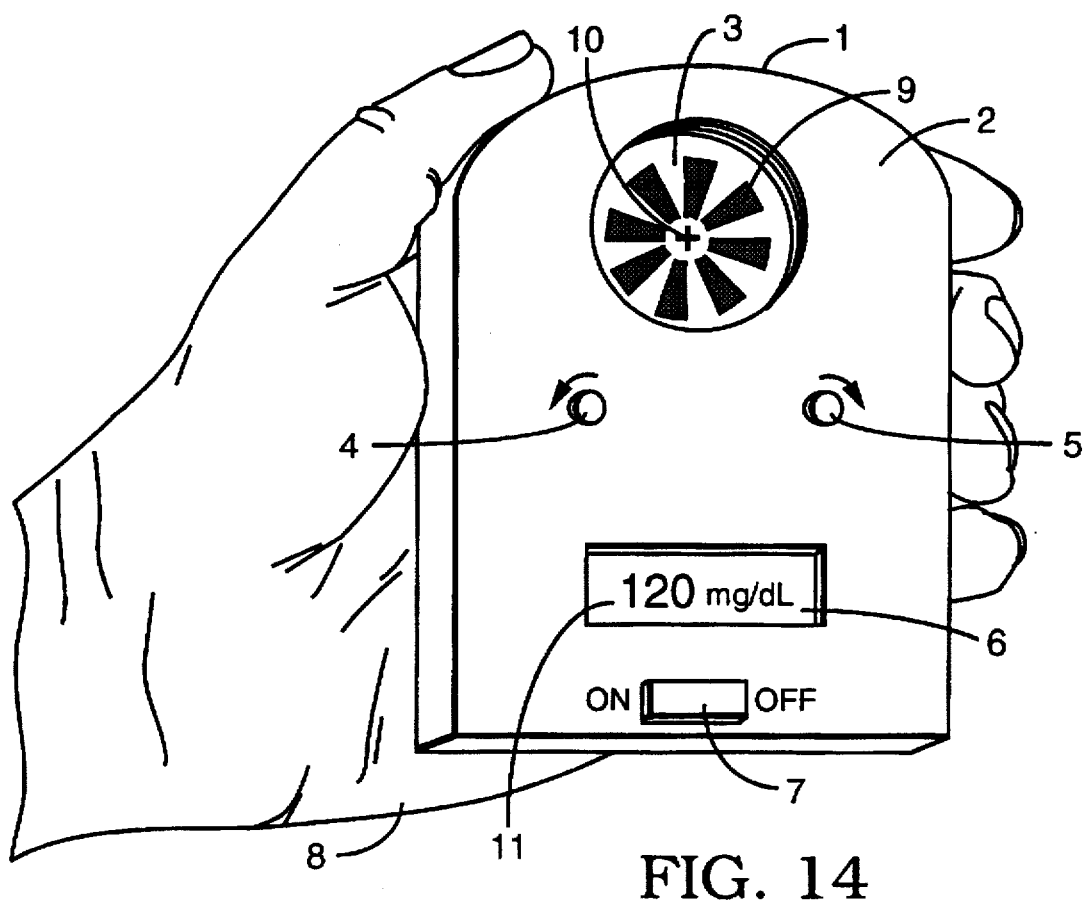
FIG. 14 shows an embodiment of the device.

A hand-held embodiment of a device 1 shown in the FIG. 14 includes a body member 2, a light pattern display 3, patient input switches 4 and 5, alphanumeric display 6 and On/Off switch 7. Other controls or input means (not shown) can provide a means for additional input from the patient, such as information regarding meals, exercise or the amount of insulin taken by the patient.

The body member 1 is preferably small enough to fit in the patient's hand 8, pocket or purse. The On/Off switch 7 turns the instrument 1 on and off. The light pattern display 3 shows the changing light pattern, for example an apparently rotating windmill wheel 9. This light pattern could be generated, for example by a combination of LEDs, diffusers, filters and lenses, by a solid state screen, by a CRT, or by any other suitable means via signals sent to the screen from a programmable microprocessor. The light pattern includes a fixation pattern 10 in its center, which the patient gazes at during a measurement, and which is used to direct the line of sight and thus control and maintain the position of the light pattern on the retina. The patient input switches 4 and 5 allow entering information about the direction of apparent rotation perceived by the patient. The alphanumeric display 6 provides information to the patient e.g., instructions and prompts during the measurement process, information regarding the quality of the measurement, the calculated blood glucose concentration, and previous measurements recalled from the memory. The characters 11 in the alphanumeric display 6 should be preferably of large enough size to be readable even by patients with reduced visual acuity.

To use the device 1, the patient turns on the instrument, looks at the fixation cross 10 in the center of the light pattern 9 and determines the initial direction of apparent rotation of the wheel. The patient then presses the input button 4 or 5 that corresponds to the direction perceived and continues to observe the pattern. When a reversal in the direction of apparent rotation is perceived, the patient presses the button 4 or 5 corresponding to the new direction of rotation and continues observing the pattern. The patient continues this process of pressing a button 4 or 5 each time the apparent rotation reverses direction, until the instrument determines (via the programmable microprocessor) that enough consistent data has been entered to compute blood glucose concentration with sufficient accuracy. The instrument uses the values of the light stimulus parameters at the times when reversals were observed to compute corresponding glucose levels, using previously entered conversion data entered during calibration as described above. The instrument then stops displaying the light pattern 9 and displays the computed blood glucose concentration in the alphanumeric display 6. If the instrument determines that it cannot compute a reliable answer, it will display one of the messages "High", "Low", or "Unable to Measure".

Figure 15:
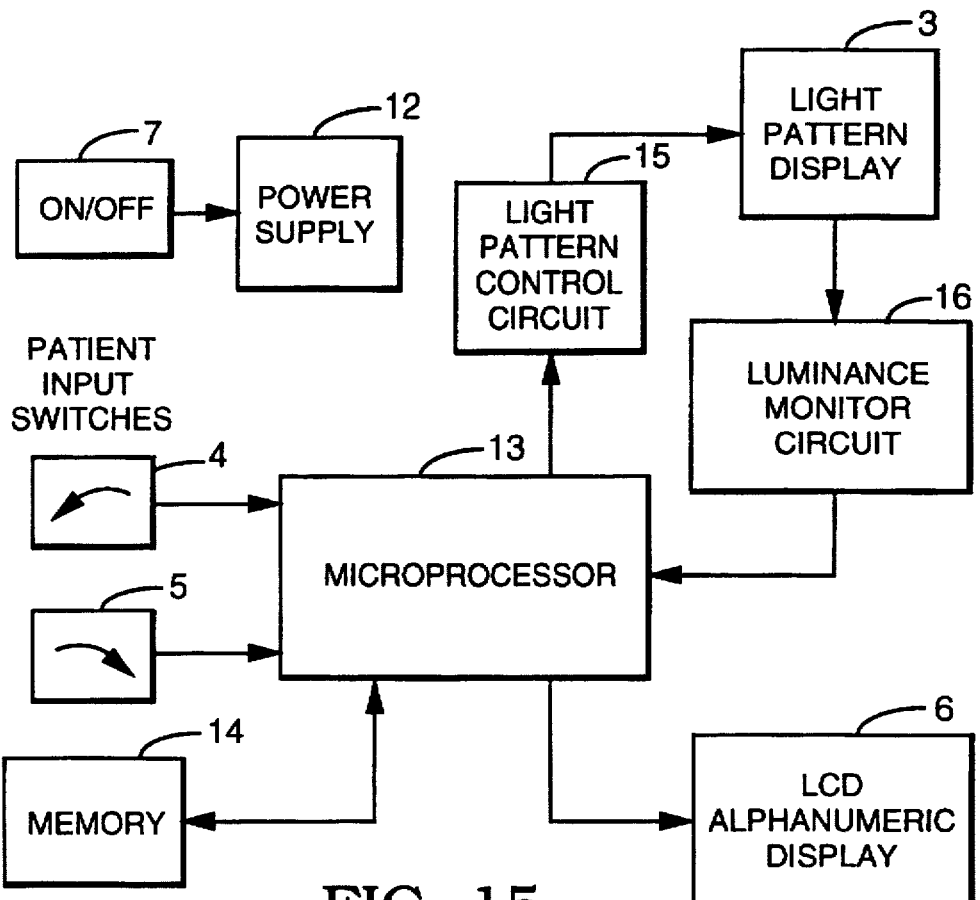
FIG. 15 is a schematic block diagram showing principal functional sections of the device of FIG. 14.

FIG. 15 is a schematic block diagram showing the principal functional sections of an embodiment including an On/Off switch 7, patient input switches 4 and 5, light pattern display 3, alphanumeric display 6, power supply 12, microprocessor 13 and associated program, memory 14, light pattern control circuit 15 and light output monitor circuit 16.

The On/Off switch 7 controls the power to the various components and starts/stops a measuring sequence. Turning on the instrument also initiates a self-diagnostic sequence that includes testing the light sources and other critical components and functions.

The light output monitor circuit 16 ensures that the light sources are functional and that their light output is within design levels. This circuit is active from the moment the instrument is turned on and throughout the measurement. The microprocessor 13 is programmed to abort the measurement and to display an informative legend in the alphanumeric display 6 if the circuit detects any fault in the light sources. This protects the user from obtaining erroneous results in the case of a failure in the operation of the light sources.

The light pattern control circuit 15 generates the sequence of the light patterns according to the specifications dictated by the microprocessor 13 and associated program.

The patient input switches 4 and 5 provide information to the microprocessor 13 as to the timing and direction of the subjective change noticed in the light pattern, e.g., the direction of apparent rotation. Each time an input switch 4 or 5 is pressed, the microprocessor 13 first checks that the correct switch has been pressed, and then reads the value of the variable light stimulus parameter existing at the moment when the switch was pressed. This parameter value information is used by the microprocessor 13 to plan the future changes in the light pattern, and to compute glucose levels, after checking for consistency of the entered data.

The microprocessor 13 executes the program, receives input from the patient input switches 4 and 5 and from the light output monitor circuit 16, reads information from, and stores information in memory 14, writes messages on the alphanumeric display 6, and provides information to the light pattern control circuit 15 about the characteristics of the light pattern to be shown on the display 3. The microprocessor can be designed and programmed in a number of different manners in accordance with programming procedures well known to those skilled in the art. The object of the microprocessor program is to efficiently utilize information provided by the user regarding the occurrence of changes in appearance of the light pattern and to coordinate all the steps, including consistency checks, repetition of stimulus presentation and calculations required to ultimately provide information to the user about the corresponding glucose level. The following section provides a specific example of a microprocessor-controlled sequence of steps that can be used to provide glucose level results, once calibration data have been entered into the memory of the device.

Measuring Sequence

Figure 16:
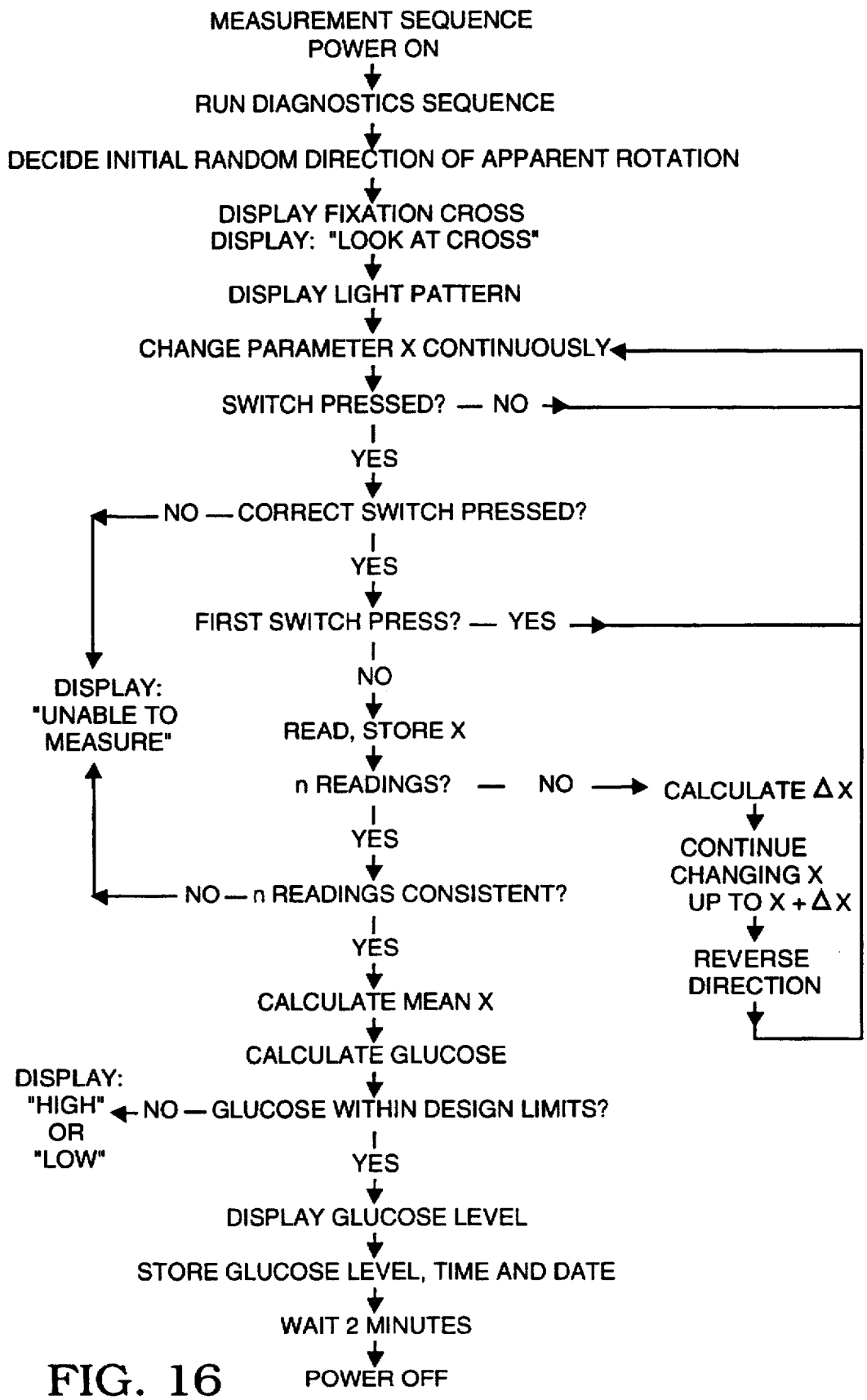
FIG. 16 is a schematic flow diagram showing steps of a diagnostic sequence.

FIG. 16 is a schematic flow diagram showing the main steps of a measuring sequence of an embodiment of the invention. This example assumes, for the sake of concreteness, that the light pattern consists of a sequence of windmill images that appear to rotate. A software program controls the execution of the sequence as is commonly done in instruments controlled by a microprocessor.

When the instrument is powered up it first goes through a diagnostics routine which tests the integrity of its main components, including the light output of the light sources.

Then the program decides randomly whether the initial direction of apparent rotation of the windmill pattern will be clockwise or counterclockwise. This direction is randomized to help avoid the possibility that the patient could influence the measurement, for example by memorizing a measurement sequence.

The light pattern is then displayed and the parameter starts to change. For example, if the light pattern consists of a sequence of windmill images that appear to rotate, the parameter change could be a gradually increasing change in luminance of a set of vanes. The change continues while the program waits for a switch press actuated by the patient.

When a switch press is detected, the program analyzes whether the correct switch has been pressed. For example, the initial conditions of the light stimulus may be such that the initial expected direction of rotation is clockwise. Thus the program expects that the clockwise switch be pressed first, and that the counterclockwise and the clockwise switches be pressed in alternation afterward. If the wrong switch is pressed, which would mean either a mistake or an inconsistent response, the device is programmed to display the message "Unable to Measure". If the correct switch was pressed, the program determines if this was the first time that the switch was pressed. If this is the case, the parameter is allowed to continue changing until the patient detects a reversal. If the switch was pressed for a second time, this means that the patient has detected the first reversal, in which case the program reads and stores the value of the changing parameter at the moment of the switch press.

Figure 17:
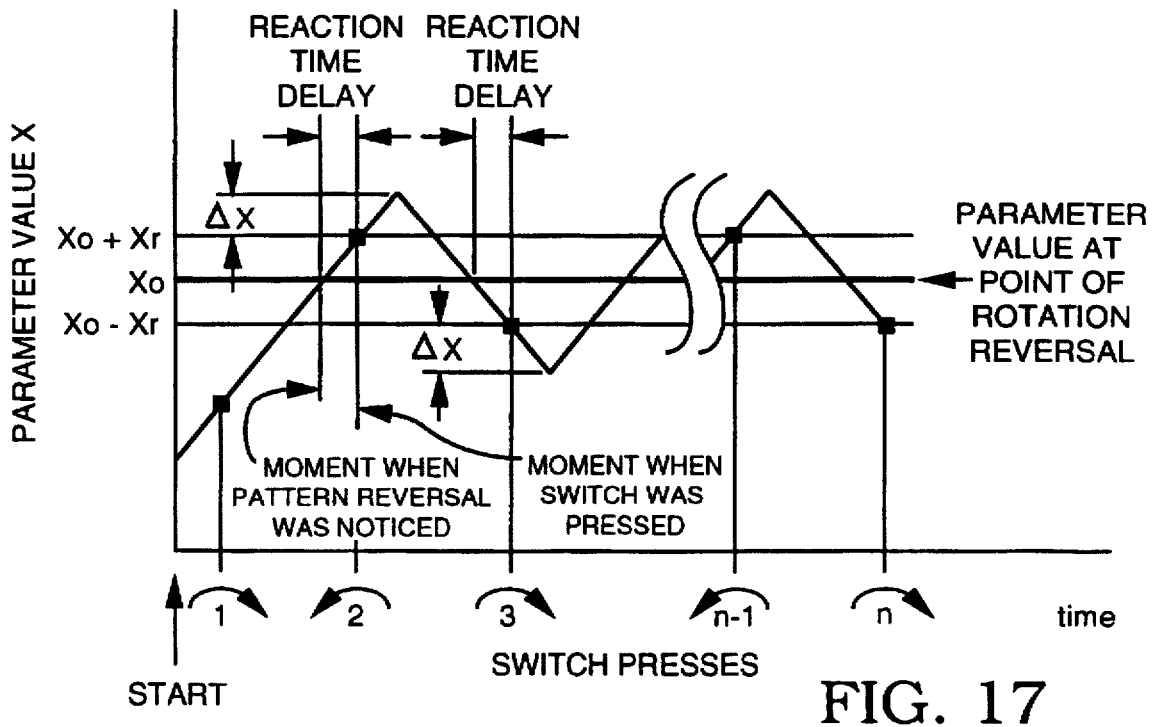

Compensation for the patient's reaction time is described with reference to FIG. 17. A time delay (reaction time) exists between the moment when the patient notes a reversal in the direction of rotation and the time when the patient presses the switch. Because of this delay, the parameter value read and recorded by the instrument when the switch was pressed ($X_o + X_r$) is slightly higher than the value at the point of reversal ($X_0$) (see FIG. 17). In order to remove this inaccuracy from the reading, a second point of reversal is measured, this time with the parameter changing in the opposite direction. In this example, after the patient pressed the switch to indicate the first reversal and the instrument recorded the parameter value $X_o + X_r$, the parameter is made to increase by the amount $\Delta X$ above $X_o + X_r$, and then it is made to decrease at the same rate until the patient notices a second reversal. When the patient presses the switch to indicate this second reversal, the program reads the current value of the parameter, which is now $X_o - X_r$. When the program later averages the recorded values ($X_o + X_r$) and ($X_o - X_r$), the error caused by the reaction time, $X_r$, will cancel out and the true value of the parameter at reversal, $X_o$, will be extracted. A smaller error will still remain owing to the fact that the number $X_r$ is not always the same, but has some statistical variation around a mean value. However, repeated pairs of measurements tend to cancel out this smaller error as well. Thus the feature of reversing the direction of parameter change several times during a measurement, cancels out the effect that the patient's reaction time could have on the measurements.

As indicated in the schematic flow diagram of FIG. 16, the program takes an even number (n) of such readings of parameter value at reversal, and then proceeds to make a consistency check of those n numbers before proceeding to calculate their average. The consistency check examines the differences between pairs of consecutive readings and determines their relative closeness. These readings should be close to each other within a factor that allows for the statistical variation of the patient's reaction time. If all the n-1 differences do not meet this criterion of closeness, the instrument cancels the reading and proceeds to display the message "Unable to Measure". This mechanism provides a safety check that prevents the possibility that either patient errors or the patient's attempts to influence the results could create erroneous readings.

Once the readings have passed the consistency check, their average is calculated. The resulting average should be close to $X_o$, the parameter value at the point of light pattern reversal, since the effect of reaction time has been removed from the measurement. This average is used to calculate corresponding glucose levels using a look up table stored in memory. The table may contain all possible pairs of appropriately rounded-off parameter values and corresponding glucose levels. Alternatively, the table may contain fewer pairs and an interpolation formula may be used to calculate intermediate values. The closest glucose level that corresponds to the averaged value of X is calculated, with an accuracy consistent with the rated accuracy of the device, for example in incremental glucose concentration units of 1 mg/dL. The pairs of parameter-glucose values will have been stored in memory at the factory, if it is determined during clinical testing that the same correspondence between parameter values and glucose levels apply to all patients. Alternatively, the numbers will be generated through a calibration procedure if it is determined that each patient requires a different correspondence between parameter values and glucose levels.

Subsequent to calculating the glucose level, the program displays the corresponding glucose value if it is within the design limits of the device; otherwise, the program displays the message "High" or "Low", depending on whether the calculated glucose value is above or below the device's design limits. The device is preferably designed to read glucose concentrations over the widest possible range, e.g., a range of 10 to 500 mg/dL with the smallest possible error, e.g., ±1%. However, a useful workable device could be designed to read over a smaller range, e.g., 40–200 mg/dL with a larger acceptable error, e.g., ±20%. Readings can be displayed in standard units used for glucose concentration, such as milligrams per deciliter(mg/dL), or millimoles per liter (mmol/L).

Lastly, the program stores the calculated glucose level in memory, along with the time and date of the measurement, for later analysis or retrieval. The program then continues to show the answer for a reasonable length of time, for example 2 minutes, and then turns itself off to preserve battery life.

This example assumed for simplicity that a single parameter in the light stimulus changed gradually. In practice, more than one parameter can change simultaneously. Multi-parameter change can provide less predictable light pattern presentations, a feature that helps avoid measurement errors caused by a patient's inconsistent responses. Multi-parameter change can also provide greater control over the range of measurement.

EXAMPLES

The following examples are put forth so as to provide those of ordinary skill in the art with a complete disclosure and description of how to carry out the methodology and make and use a device of the invention and are not intended to limit the scope of what is regarded as the invention. Efforts have been made to ensure accuracy with respect to numbers used (e.g., luminance levels, glucose levels, times, etc.) but some experimental errors and deviations should be accounted for.

Example 1

Figure 4:
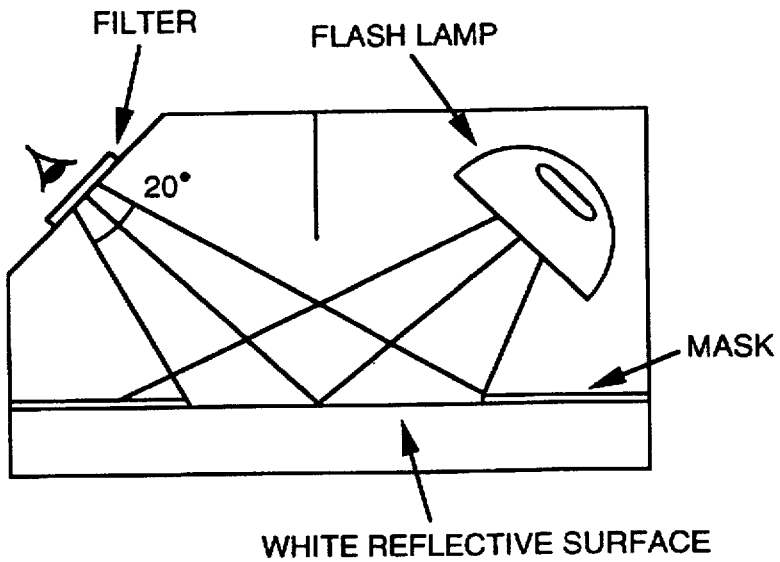
FIG. 4 is a schematic view of the arrangement of components and the viewer being tested in a particular embodiment of the invention.
Figure 5:
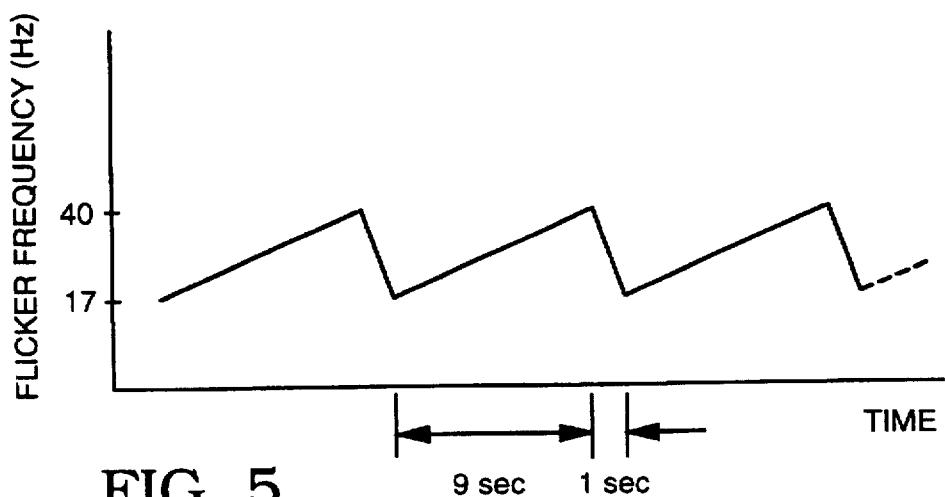
FIG. 5 is a graph relating flicker frequency to time.
Figure 6:
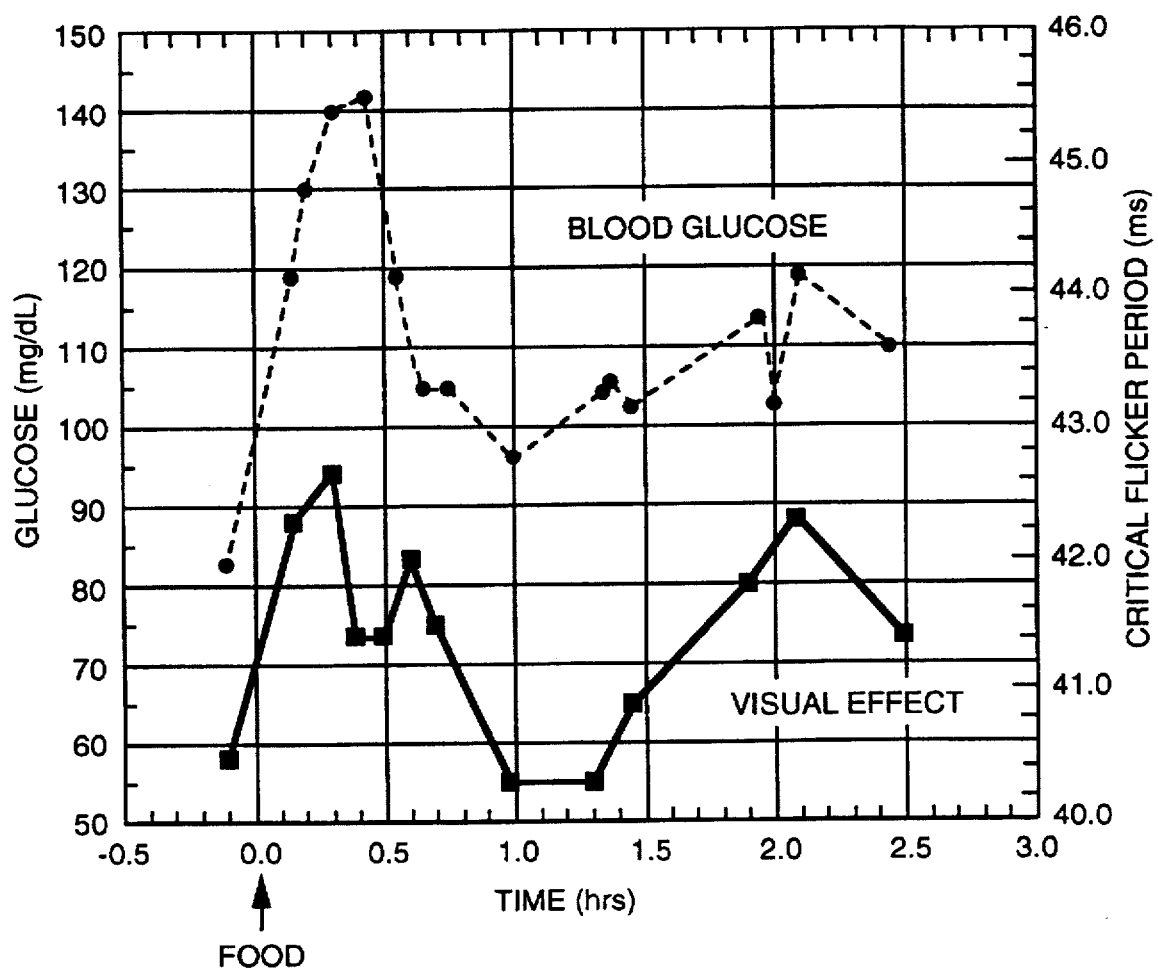
FIG. 6 is a graph relating glucose level to time.
Figure 7:
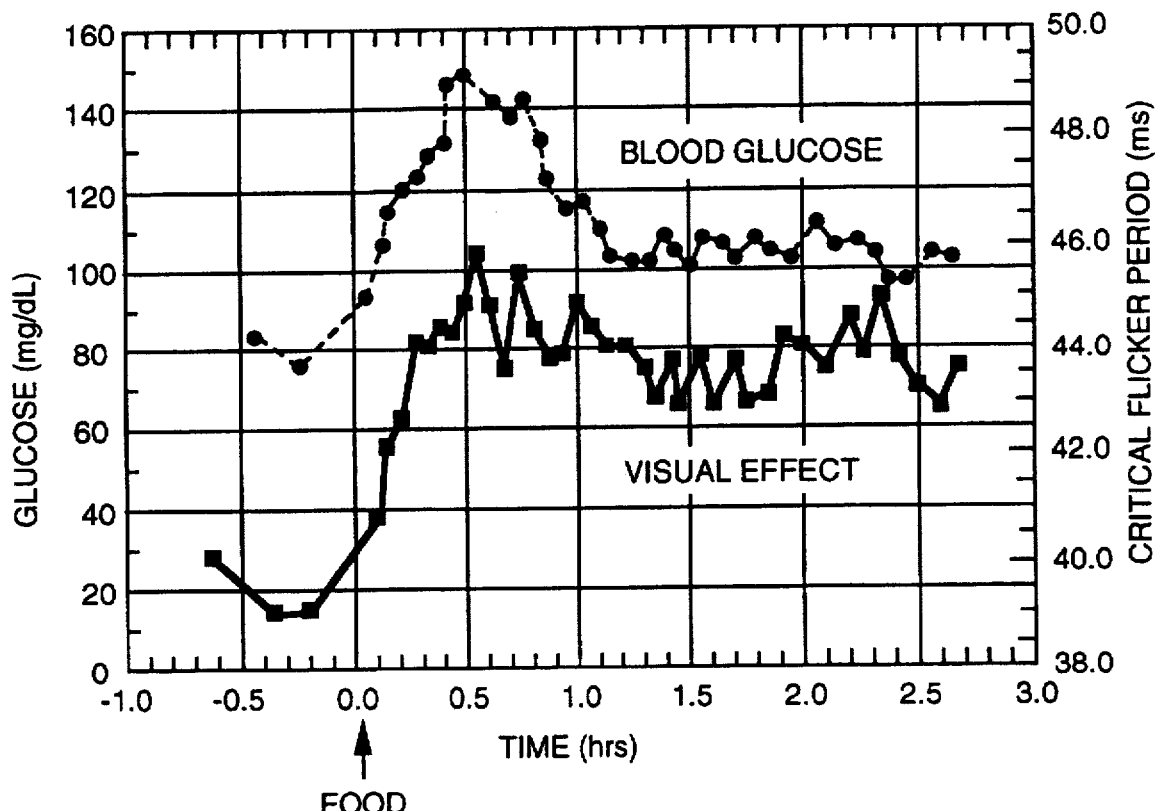
FIG. 7 is a graph relating glucose level to time.
Figure 8:
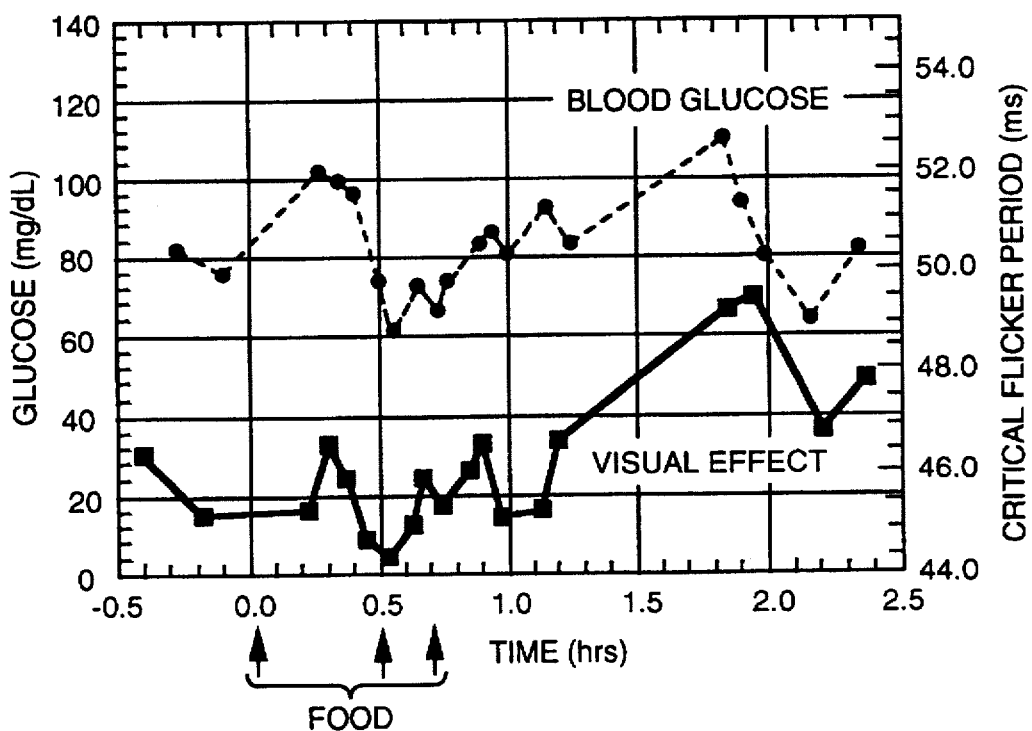
FIG. 8 is a graph relating glucose level to time.
Figure 9:
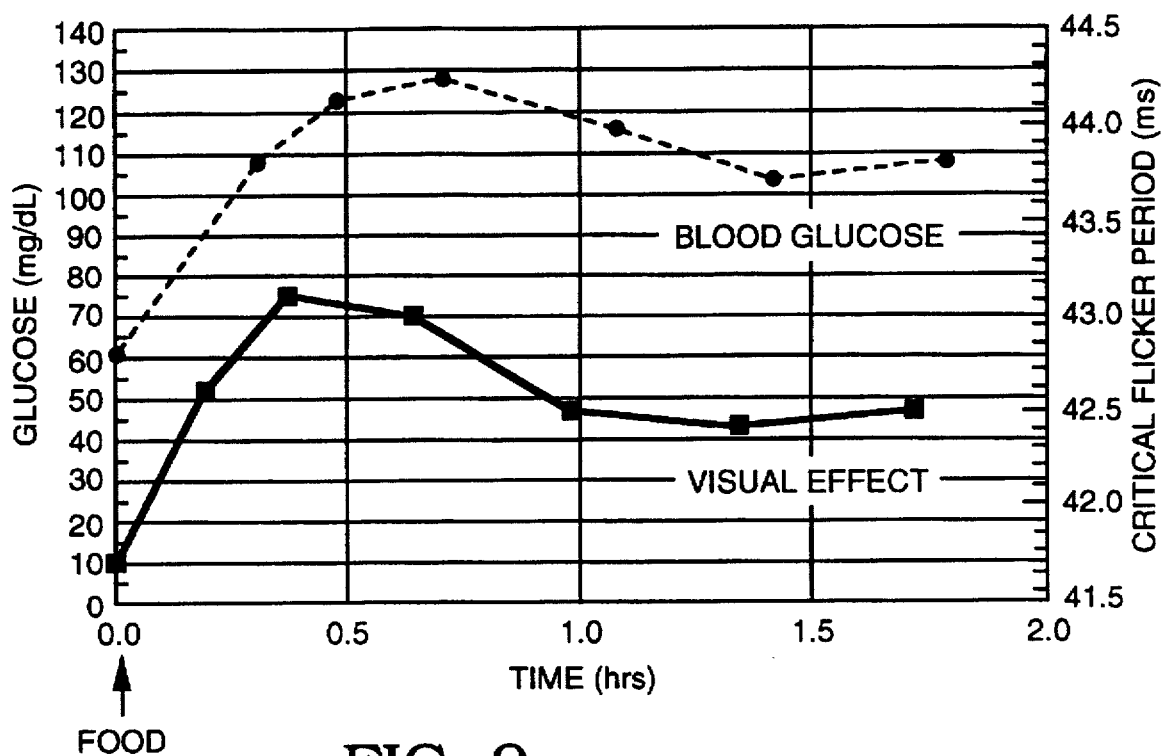
FIG. 9 is a graph relating glucose level to time.
Figure 10:
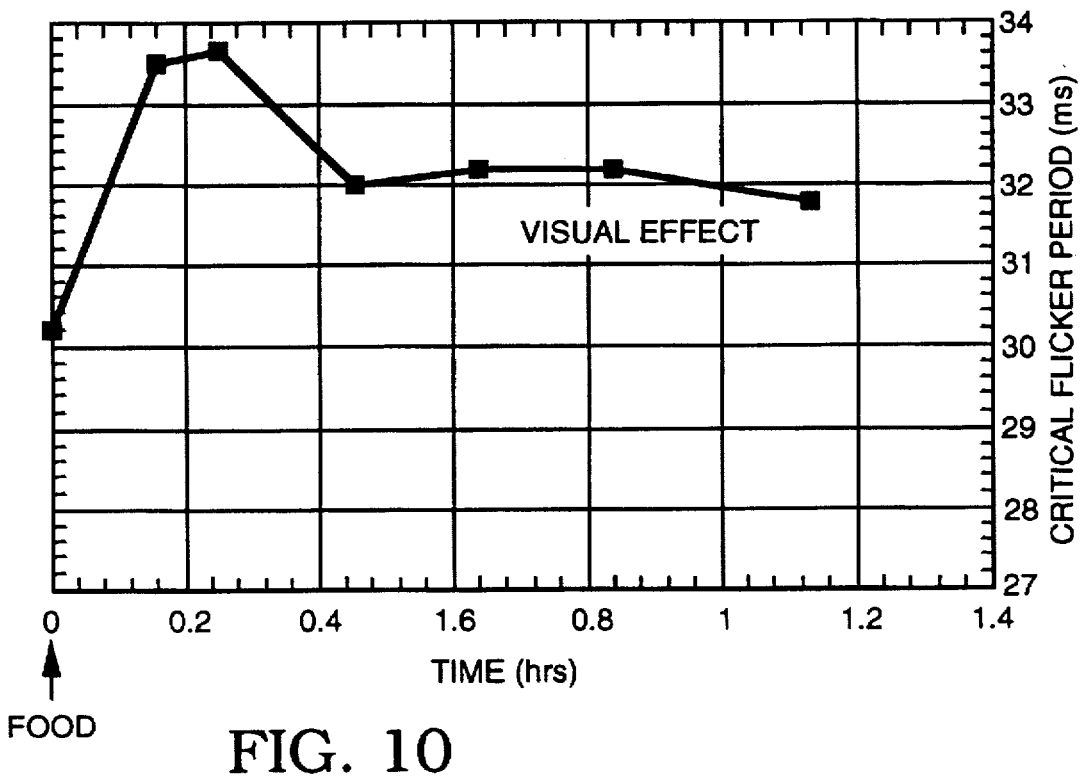
FIG. 10 is a graph relating critical flicker period to time.

A test device as shown in FIG. 4 was used to create a series of light pulses having a variable frequency as shown in the graph of FIG. 5. The frequency of the light pulses was set to change over time as shown within FIG. 5. Specifically, the series of light pulses increased in frequency linearly from 17 Hz to 40 Hz over 9 seconds. Thereafter, the pattern of light pulses decreased in frequency from 40 Hz to 17 Hz in 1 second. The light source was a flash lamp controlled by a signal generator. Each light pulse had an exponential time course with a time constant of 5 milliseconds. The pulses illuminated a diffuser which produced a peak luminance of 800 cd/m². The illuminated area was in the form of a white reflective surface bordered by a black mask. The reflective surface was positioned relative to the patient's field of view so that the surface took up 20° of visual field. Light reflected off of the white reflective surface could enter the eye of the user only via a red Wratten filter which allows the transmission of wavelengths of above 610 nanometers. The subject viewed the field monocularly and fixated the line of sight at the center of the illuminated field.

The light pattern consisting of a flickering light caused a perceived characteristic in the pattern consisting of a subtle impression of radial movement. The direction of this radial movement varies with the frequency of flicker. The apparent movement is caused by a combination of two effects. First, the M-system transmits signals faster than the P-system. Second, while the P-system is most sensitive at the center of the retina the M-system becomes more sensitive towards the periphery. The result is that lower frequencies, which stimulate preferentially the P-system, create an impression of movement away from the center of the retina. However, higher frequencies, which stimulate the M-system preferentially, create an impression of movement towards the center. In short low frequencies cause apparent movement from the center towards the periphery and high frequency flicker creates a perception of movement from the periphery towards the center. An intermediate frequency in the range of 20 Hz to 25 Hz causes the apparent movement to stop for an instant before starting to move in the opposite direction.

Three subjects with normal glucose metabolism and vision were tested with the device. Two of the three subjects did not know the purpose of the experiment, or what was changing or being measured in the light stimulus. All subjects were required to press the switch when they noticed that the radial movement stopped before reversing direction. A computer was programmed to read the instantaneous flicker frequency when the subject pressed the switch. The inverse of the flicker frequency, the flicker period, was stored in memory for later analysis. Each measurement took 10 seconds to complete. The average of ten such measurement was recorded automatically as the "critical flicker period" measurement. The subjects had no knowledge of the measurement values during the experiment.

In each experiment, the subject's blood glucose level was manipulated with a glucose load in the form of a normal meal following at least 6 hours of fasting. Critical flicker period measurements were made at regular intervals—every 10 to 30 minutes—starting before the meal and continuing for at least 1 hour and at most 2.5 hours after the meal. In close time proximity with these measurements, blood glucose was measured with a conventional home-use invasive blood glucose monitor, specifically a LifeScan One Touch II™ Glucose Meter.

The results obtained with different subjects are shown within FIGS. 6, 7, 8, 9 and 10 wherein each of these figures corresponds to one experiment carried out on one subject. Each graph shows two plots: the upper plot shows the time course of the blood glucose measurements in the subject, while the lower plot shows the time course of the critical flicker period measurements for the same subject, except in FIG. 10, that corresponds to an experiment in which blood glucose was not measured.

The plots shown within all of the FIGS. 6–10 show that glucose measurements and critical flicker period measurements follow a parallel time course after a glucose load. Even FIG. 10, in which glucose measurements are absent, the time course of the critical flicker period follows the expected glucose time course. Thus the value of the flicker period when the subject noticed the stopping of the radial movement, changed in parallel with changes in blood glucose level. Expressed in more general terms, the value of the variable parameter in the light pattern at the moment when the observer noticed the subjective visual effect, (critical parameter value) changed in parallel with changes in blood glucose. These results are consistent with the assumptions presented earlier, that the subjective visual effect is associated with the M-P crossover point, and that the M-P crossover point shifts in parallel with changes in glucose level. This example demonstrates that it is possible to monitor blood glucose levels by monitoring changes in the critical parameter value, which is the essence of the present invention.

Further experimentation was carried out using a total of twelve subjects, each of whom viewed the changing light stimulus in the form of changing rate of flicker as described above. It was found that only five of the twelve subjects could consistently detect the visual effect associated with the M-P crossover point. Thus, the variable light flicker effect can be consistently used with certain subjects but not consistently used with all subjects in order to monitor glucose levels.

Example 2

Although the results of Example 1 demonstrate the utility of the present invention, different changing light stimuli need to be provided in order to demonstrate universal applicability of the present invention. Towards that end reference is made to FIGS. 11 and 12 which are images referred to as windmill patterns or windmills. Light patterns with circular symmetry such as the windmill patterns shown in FIGS. 11 and 12 have been found to provide a very clear visual effect that is observable by all individuals. Such patterns will be referred to as windmill patterns, but they could be designed in a variety of shapes and could resemble cart wheels, automobile tires, or any object of circular symmetry, as long as it contains components that can be changed from one frame to the next in such a manner as to create the appearance of rotation.

Figure 11:
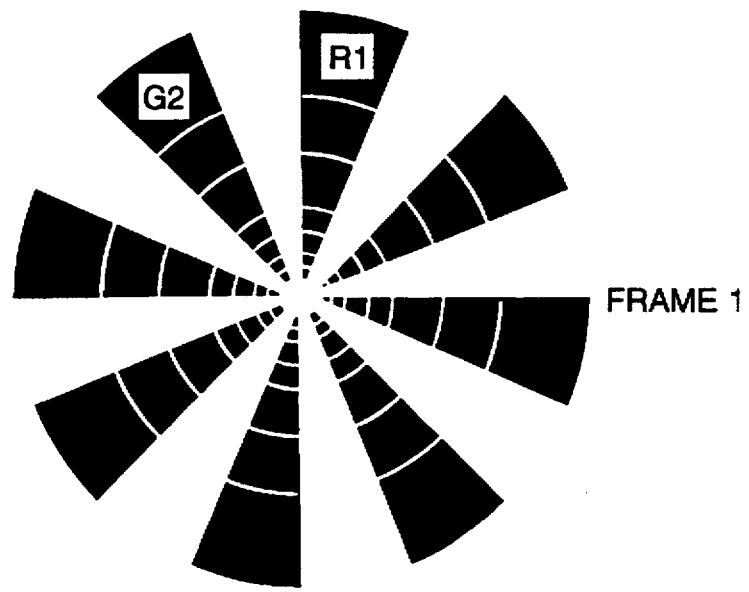
FIG. 11 is a black and white schematic view of a windmill light stimulus in a first position.
Figure 12:
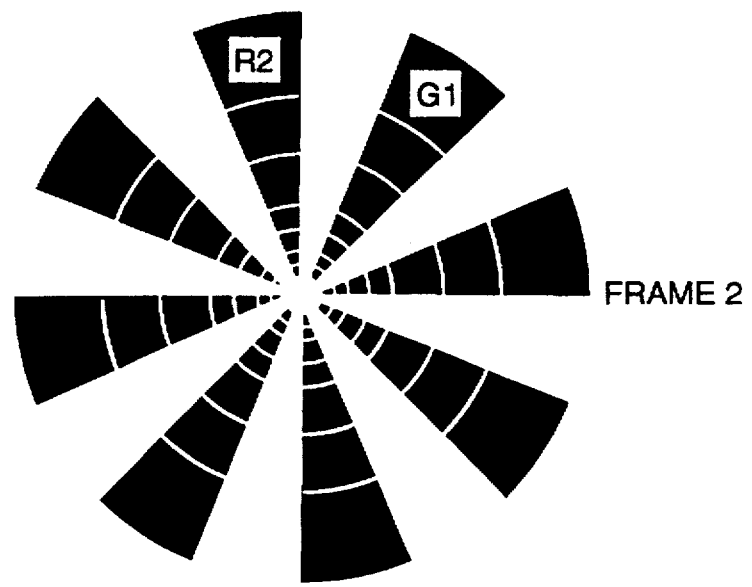
FIG. 12 is a black and white schematic view of a windmill light stimulus in a second position.

The specific example of a windmill pattern that has been used for experimentation is depicted in FIGS. 11 and 12 and each contain 8 vanes of alternating colors. Thus, as shown in FIG. 11 the vanes in frame 1 are colored R1, G2, R1, G2, etc., whereas as shown in FIG. 12 the vanes in frame 2 are colored R2, G1, R2, G1, etc. An image such as that shown in FIG. 11 is presented on a screen. That image disappears and is quickly replaced with an image such as that shown in FIG. 12. As with the images of a motion picture one image disappears and is quickly replaced by another. By careful choice of the 4 colors R1, G2, R2 and G1, it is possible to create an impression of continuous rotation. Although only 2 frames are shown in FIGS. 11 and 12, a total of 4 frames are required to create the impression of smooth and continuous rotation: frame 3 looks similar to frame 1 but has the vane colors switched relative to the colors of frame 1 (G2 vanes should be R1 and vice versa), and frame 4 looks as frame 2 but has the vane colors switched relative to the colors of frame 1 (R2 vanes should be G1 and vice versa). In practice the sequence of 4 frames is presented repeatedly as a continuous loop, or a "movie", at a rate of, for example, 1 frame per second or up to 40 frames per second, so that the impression of continuous rotation continues for the desired length of time, for example 10 to 30 seconds. The continuous rotation can be clockwise or counterclockwise, depending on the choice of vane colors. For example, if R2 is similar to R1, and G1 is similar to G2, the windmill appears to rotate counterclockwise. On the other hand, the windmill appears to rotate clockwise if G1 is similar to R1 and R2 is similar to G2. It is possible to change one or several parameters of the windmill pattern, for example the color or luminance of the vanes, or the color or the luminance of the background, as the sequence of frames is being presented. The windmill images are specifically designed and are changed in a particular manner so as to stimulate the M- and P-systems in sequence while creating a profound visual effect at the M-P crossover point. Specifically, the windmill appears to reverse direction at the M-P crossover point. The image can be created and controlled by a personal computer with the image being generated on a computer monitor. However, the image can be shown on a much smaller screen and generated by a small dedicated programmable microprocessor unit contained within a hand-held device which also includes the screen where the image is shown.

Although the operability of the device and method of the present invention does not depend on the exact mechanism responsible for the apparent rotation of the windmill pattern, the following explanation is provided so that those skilled in the art can understand the physiological mechanism that produces the apparent rotation effect and its reversal. When the image is in the form of a windmill as per FIGS. 11 and 12 and the frame changes from FIG. 11 (frame 1) to FIG. 12 (frame 2) it appears to the eye that the vane labeled R1 has moved either to R2 or to G1, depending on whether R2 or G1 appears more similar to R1. In one particular embodiment R2 is set to match R1 in color but not in luminance. Further, G1 is set to match R1 in luminance but not in color. Thus, for example, in frame 1, R1 could be a bright red color, and G2 could be a dim green, whereas in frame 2, R2 could be a dim red and G1 a bright green. Thus in this example, the red vane in frame 2, R2, matches R1 in color but not in brightness, whereas the green vane in frame 2, G1, matches R1 in luminance but not in color. With these particular settings the cells of the M-retinal system are stimulated by the mismatch in luminance between R1 and R2 and convey the message "luminance mismatch detected here therefore rotation is not counterclockwise." Simultaneously, cells of the P-system are in direct competition with the cells of the M-system for detecting the direction of rotation of the windmill. The cells of the P-system are stimulated by the color mismatch between R1 and G1. Upon detection of this mismatch the cells forward a message "color mismatch detected, therefore rotation is not clockwise." If the luminance mismatch between R1 and R2 is greater than the color mismatch between R1 and G1, the M-system will be stimulated more than the P-system, and the signal sent from the M-retinal system cells, "not counterclockwise", will prevail and the apparent movement will be clockwise. However, in the opposite situation in which the color mismatch is greater than the luminance mismatch, the cells of the P-retinal system will be stimulated more than the cells of the M-system, therefore the signal sent by the P-system, "not clockwise", will dominate and the apparent direction of rotation will be counterclockwise. Apparent rotation reversal can also occur not only when the luminance or color of the vanes changes, but also when the background luminance changes over time. The mechanism for this effect is more complex and is related to the fact that the presence of a background affects the apparent color and luminance of the vanes; thus it is possible to manipulate the apparent color and luminance of the vanes indirectly, by changing the color and/or the luminance of the background in a specific manner.

Based on the above it can be seen that both the M- and the P-systems are used by the visual system to judge similarities in the color and luminance of a sequence of vanes of a windmill pattern in order to judge direction of rotation. Since the P-system is more sensitive to color changes and the M-system is more sensitive to luminance changes, controlling the color and or luminance of the components of the sequential frames of the windmill can change the relative stimulation of the M- and P-systems. Depending on which system receives greater stimulation the viewer will perceive rotation in the counterclockwise or clockwise direction. The direction of rotation will continue as long as the original dominant system continues to dominate. However, when the parameters are changed so that the other system dominates the direction of rotation will appear to reverse itself. The point at which the direction of rotation appears to reverse itself is the M-P crossover point. When the viewer notices this point the device is actuated in order to make note of the parameters being projected at this point i.e., the color and luminance of the various components of the windmill. As indicated above in Example 1 the blood glucose level of the individual being tested is then determined by a conventional means. The process is repeated numerous times at various glucose levels over a range in order to calibrate the device. After calibration has taken place the viewer can determine his own glucose level by merely viewing the sequence of apparently rotating windmill patterns and noting the point at which the direction of rotation reverses itself.

Figure 13:
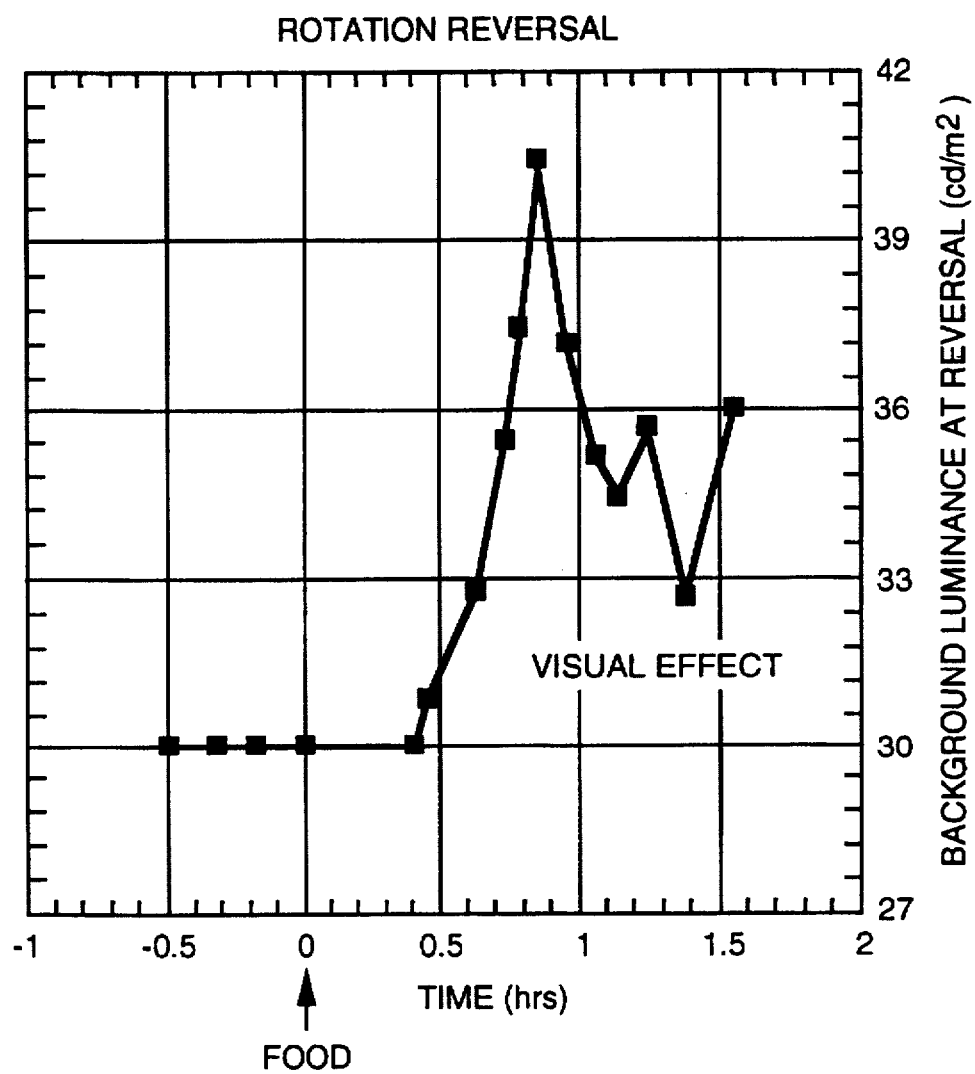
FIG. 13 is a graph relating background luminance at the point of rotation reversal of the windmill light stimulus to time.

A windmill pattern similar to the one described above and shown in FIGS. 11 and 12 was tested using a computer screen and projecting sequential frames or a "movie" of windmill images onto the computer screen at a rate of 1 frame every 0.5 seconds. The windmill outer diameter was 18 mm and was viewed at 508 mm distance, which produced a retinal image 2.25 degrees in diameter. The colors of the windmill vanes were as follows: the R1 and R2 vanes were identical, and consisted of a pure red phosphor emission of the CRT screen, with CIE coordinates x=0.63, y=0.34 and luminance 44 $cd/m^2$. The G1 and G2 vanes were also identical to each other, consisted of pure green phosphor emission with CIE coordinates x=0.28, y=0.60, and were set to a luminance level of 44 $cd/m^2$. The background consisted of a rectangular area 25 mm in diameter, surrounding the windmill and filling the clear spaces in each windmill image. The background color was white, and consisted of a balanced mixture of red, green and blue phosphors, and had CIE coordinates x=0.28, y=0.30. The luminance of the background was set to decrease gradually, from 42 $cd/m^2$ to 30 $cd/m^2$ in 40 seconds, in steps of 0.3 $cd/m^2$ at a rate of one step every second. Thus, in this example the variable parameter was the background luminance. This slow rate of change of the variable parameter prevented any effect of the subject's reaction time (time delay between noticing the rotation reversal and pressing the key) on the measurement. This is because reaction times, which have been measured in separate experiments as being from 0.3 to 0.5 seconds long, are shorter than the time it takes for the variable parameter to change one step (1 second). The above-specified parameters for the windmill and the background were such that when the movie started playing at the high background luminance, the sequence of windmill images caused a clear impression of counterclockwise rotation. This impression of rotation continued up to a point, when as a result of the background luminance level decreasing gradually, the rotation suddenly appeared to reverse to a clockwise direction. The gradual drop in the background luminance level occurs at such a slow rate that the subject is not aware of a change in the appearance of the windmill or of the background; the subject is only aware of a clear rotation, which is counterclockwise at the beginning, and at some point reverses suddenly and becomes clockwise rotation, and then continued to be clockwise rotation until the end of the movie, when the background luminance level reached its minimum value of 30 cd/m². The subject observed the apparently-rotating windmill pattern from the beginning of the movie, when the background luminance was 42 cd/m², and as the movie progressed and the background luminance decreased gradually the subject continued to observe the pattern until the point when the subject noticed a reversal in the direction of apparent rotation of the windmill, from counterclockwise to clockwise, at which point the subject pressed a key on the computer keyboard. The computer then stopped the movie and displayed the value of the background luminance at the moment when the subject pressed the key, or "critical background level" The entire process took between 10 and 40 seconds. The subject was given a glucose load consisting of a normal meal following at least 6 hours of fasting. Measurements of the critical background level were made approximately every 6 to 10 minutes in the manner explained above. The measurements started 0.5 hours before the meal and continued for 1.5 hours after the meal. The results obtained are shown in FIG. 13. Blood glucose levels were not measured in this experiment by conventional means. However, results obtained show that the critical background levels changed with time and that the time course of these changes followed the expected changes in the subject's blood glucose levels. These results demonstrate that for a light pattern consisting of the windmill pattern with variable background described above, the critical parameter level, or value of the variable parameter when the observer noticed the subjective visual effect—in this case the reversal in the direction of apparent rotation—changed in parallel with changes in blood glucose. Per the explanation advanced earlier regarding the mechanism that produces apparent rotation and its direction reversal, the results of this experiment are consistent with the assumptions that the subjective visual effect is associated with the M-P crossover point, and that the M-P crossover point shifts in parallel with changes in glucose level.

The instant invention is shown and described herein in what is considered to be the most practical, and preferred embodiments. It is recognized, however, that departures may be made therefrom which are within the scope of the invention, and that obvious modifications will occur to one skilled in the art upon reading this disclosure.

I claim:

1. A method of determining a blood glucose level of a human subject, comprising:

providing a light pattern which provides a greater amount of stimulation to a first retinal system relative to a second retinal system, resulting in a first:second stimulation ratio greater than one;

perceiving in the light pattern a characteristic that results from different sensitivities of the first retinal system and the second retinal system to the light pattern; and determining a blood metabolite level of said subject from the perceived characteristic in the light pattern resulting from different properties of the first retinal system and the second retinal system.

2. The method of claim 1, wherein the first retinal system is an M-retinal system and the second retinal system is a P-retinal system.

3. A method of determining a blood glucose level of a person, comprising:

observing a light pattern having a parameter which changes gradually over time;

perceiving in the light pattern a subjective visual effect; and indicating a blood glucose level of the person observing the light pattern from the light pattern parameter.

4. The method of claim 3, wherein at least a portion of the light pattern changes over time with respect to a parameter selected from the group consisting of color, luminance level, contrast, shape, size, detail content, texture, speed of movement, direction of movement and rate of flicker.

5. The method of claim 3, wherein the changing light pattern stimulates a first retinal system and a second retinal system.

6. The method of claim 5, wherein the changing light pattern stimulates two retinal systems which respond differently relative to each other with respect to changes in the light pattern and with respect to changes in blood glucose concentration.

7. The method of claim 6, wherein the changing light pattern stimulates the first retinal system and the second retinal system in a gradually changing ratio with respect to each other.

8. The method of claim 5, wherein the first retinal system is an M-system and the second retinal system is a P-system.

9. A method of determining a blood glucose level of a person having M-system and P-system retinal systems, comprising:

observing a light pattern which changes over time with respect to at least one parameter and which stimulates the M-retinal system and the P-retinal system in a changing ratio;

perceiving in the light pattern a subjective visual effect; and relating a value of a changing parameter in the light pattern when the subjective visual effect is perceived to a blood glucose level of the person observing the light pattern.

10. The method of claim 9, wherein the subjective visual effect represents a predetermined measured degree of relative stimulation of the M-retinal system and the P-retinal system.

11. The method of claim 9, wherein the subjective visual effect occurs at M-P crossover point.

12. The method of claim 9, wherein the light pattern changes over time with respect to a characteristic selected from the group consisting of color, luminance level, contrast, shape, size, detail content, texture, speed of movement, direction of movement and rate of flicker.

13. The method of claim 12, wherein the light pattern consists of a flickering light, and the subjective visual effect is a visual effect selected from the group consisting of appearance of colors, appearance of a regular geometric pattern and cessation of radial movement.

14. The method of claim 9, wherein the light pattern is selected from the group consisting of a series of windmills and wheel images, and the subjective visual effect is a reversal in the direction of rotation of the light pattern.

15. A device for measuring the glucose level of a person, comprising:

a body member; and a means for generating a light pattern connected to the body member, wherein the light pattern stimulates a first retinal system and a second retinal system in a manner such that an observer will note a subjective visual characteristic in the light pattern which indicates a known blood glucose level of the person.

16. The device of claim 15, wherein the first retinal system is an M-retinal system and the second retinal system is a P-retinal system.

17. The device of claim 16, wherein the subjective visual characteristic is direction of apparent rotation.

18. A device for determining the blood glucose level of a person, comprising:
- a body member;
- a means for generating a changing light pattern that changes over time with respect to at least one parameter, wherein the light pattern changes in a controlled manner and stimulates two complementary retinal systems in a continuously changing ratio of stimulation;
- an actuation means which is actuated to indicate the presence of a subjective visual effect, and which initiates measurement of the parameter as the light pattern when actuated;
- a microprocessor comprising a memory and software programming, which relates measured parameter values to a predetermined blood glucose level; and
- a means for displaying information about blood glucose levels.

19. The device of claim 18, wherein the light pattern changes over time with respect to one or several parameters selected from the group consisting of color, luminance level, contrast, shape, size, detail content, texture, speed of movement, direction of movement and rate of flicker.

20. The device of claim 19, wherein the light pattern comprises a flickered light of variable flicker rate.

21. The device of claim 19, wherein the light pattern comprises a series of images which create a windmill or wheel pattern that appears to rotate.

22. The device of claim 18, wherein the two complementary retinal systems comprise an M-retinal system and a P-retinal system, and said changing ratio of stimulation passes through a point where the M-retinal system and the P-retinal systems are stimulated equally.

23. The device of claim 18, wherein the microprocessor includes information on a range of parameter values associated with the presence of a subjective visual effect, along with corresponding blood glucose levels.

24. The device of claim 18, wherein the microprocessor is programmed to avoid erroneous measurements by making redundant measurements, checking the consistency of the user's responses and canceling any effect created by user's reaction time.

25. The device of claim 18, wherein the microprocessor is programmed to avoid erroneous measurements by continuously diagnosing and testing components of the device and aborting measurement to avoid anomalous results.

* * * * *